US011179416B2

(12) United States Patent
Sharma et al.

(10) Patent No.: US 11,179,416 B2
(45) Date of Patent: Nov. 23, 2021

(54) COMPOSITION AND METHOD FOR TREATING OSTEOARTHRITIS WITH MANGANESE DIOXIDE NANOPARTICLES

(71) Applicant: UNIVERSITY OF FLORIDA RESEARCH FOUNDATION, INCORPORATED, Gainesville, FL (US)

(72) Inventors: Blanka Sharma, Gainesville, FL (US); Isaac Adjei, Gainesville, FL (US); Shreedevi Kumar, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/971,399

(22) PCT Filed: Feb. 20, 2019

(86) PCT No.: PCT/US2019/018699
§ 371 (c)(1),
(2) Date: Aug. 20, 2020

(87) PCT Pub. No.: WO2019/164892
PCT Pub. Date: Aug. 29, 2019

(65) Prior Publication Data
US 2020/0390806 A1 Dec. 17, 2020

Related U.S. Application Data

(60) Provisional application No. 62/632,873, filed on Feb. 20, 2018.

(51) Int. Cl.
*A61K 33/32* (2006.01)
*A61P 19/02* (2006.01)
(Continued)

(52) U.S. Cl.
CPC ............ *A61K 33/32* (2013.01); *A61K 9/0019* (2013.01); *A61K 9/1641* (2013.01); *A61K 9/1694* (2013.01); *A61P 19/02* (2018.01)

(58) Field of Classification Search
CPC .... A61K 33/32; A61K 48/00; A61K 2300/00; A61K 35/28; A61K 35/32; A61K 9/0019;
(Continued)

(56) References Cited

U.S. PATENT DOCUMENTS

| | | | |
|---|---|---|---|
| 2014/0212335 A1* | 7/2014 | Lee | A61L 2/00 422/30 |
| 2017/0252440 A1 | 9/2017 | Wu et al. | |
| 2020/0390806 A1 | 12/2020 | Sharma et al. | |

FOREIGN PATENT DOCUMENTS

WO   2019164892 A1   8/2019

OTHER PUBLICATIONS

Rosenbaum, Cathy Creger et al., "Antioxidants and Antiinflammatory Dietary Supplements for Osteoarthritis and Rheumatoid Arthritis", Alternative Therapies, Mar./Apr. 2010, vol. 16, No. 2, pp. 32-40.

(Continued)

*Primary Examiner* — Ernst V Arnold
(74) *Attorney, Agent, or Firm* — Timothy H. Van Dyke; Wolter, Van Dyke, Davis, PLLC

(57) ABSTRACT

The present disclosure relates to manganese dioxide nanoparticles and their use in treatment of oxidative stress and conditions related to or characterized by oxidative stress, including osteoarthritis.

21 Claims, 15 Drawing Sheets

Specification includes a Sequence Listing.

(51) Int. Cl.
A61K 9/00 (2006.01)
A61K 9/16 (2006.01)

(58) Field of Classification Search
CPC ...... A61K 9/14; A61K 9/1641; A61K 9/1694; A61K 47/32; A61L 2400/06; A61L 2400/12; A61L 2430/24; A61L 27/047; A61P 19/02
See application file for complete search history.

(56) References Cited

OTHER PUBLICATIONS

Rothenfluh, Dominique A. et al., "Biofunctional polymer nanoparticles for intra-articular targeting and retention in cartilage", Nature Materials, Mar. 2008, vol. 7, pp. 248-254.
Rousset, Francis et al., "Heme Oxygenase-1 Regulates Matrix MetalloproteinaseMMP-1 Secretion and Chondrocyte Cell Death via Nox4 NADPH Oxidase Activity in Chondrocytes", PLOS ONE, Jun. 2013, vol. 8, issue 6, e66478, 13 pages.
Song, Manli et al., "Bioconjugated Manganese Dioxide Nanoparticles Enhance Chemotherapy Response by Priming Tumor-Associated Macrophages toward M1-like Phenotype and Attenuating Tumor Hypoxia", American Chemical Society, 2016, vol. 10, pp. 633-647.
Takada, Tsuyoshi et al., "Bach1 deficiency reduces severity of osteoarthritis through upregulation of heme oxygenase-1", Arthritis Research & Therapy, 2015, vol. 17, No. 285, 11 pages.
Tan, Hor-Yue et al., "The Reactive Oxygen Species in Macrophage Polarization: Reflecting Its Dual Role in Progression and Treatment of Human Diseases", Oxidative Medicine and Cellular Longevity, 2016, vol. 2016, Article ID 2795090, 16 pages.
Tootoonchi, Mohammad Hossein et al., "Manganese oxide particles as cytoprotective, oxygen generating agents", Acta Biomaterialia, 2017, vol. 59, pp. 324-337.
Torzilli, Peter A. et al., "Effect of Proteoglycan Removal on Solute Mobility in Articular Cartilage", J. Biomechanm, 1997, vol. 30. No. 9, pp. 895-902.
Whitmire, Rachel E. et al., "Self-assembling nanoparticles for intra-articular delivery of anti-inflammatory proteins", Biomaterials, 2012, vol. 33, pp. 7665-7675.
Yan, Huimin et al., "Suppression of NF-κB activity via nanoparticle-based siRNA delivery alters early cartilage responses to injury", PNAS, May 9, 2017, vol. 114, No. 19, E6199-E6208, 11 pages.
Zhang, Mei et al., "MnO2-Based Nanoplatform Serves as Drug Vehicle and MRI Contrast Agent for Cancer Theranostics", ACS Appl. Mater. Interfaces, 2017, vol. 9, pp. 11337-11344.
Zhu, Wenwen et al., "Modulation of Hypoxia in Solid Tumor Microenvironment with MnO2 Nanoparticles to Enhance Photodynamic Therapy", Adv. Funct. Mater., 2016, vol. 26, pp. 5490-5498.
PCT/US2019/018699, PCT Search Report & Written Opinion, dated Jun. 18, 2019, 12 pages.
Abbasi, Azhar Z. et al., "Hybrid Manganese Dioxide Nanoparticles Potentiate Radiation Therapy by Modulating Tumor Hypoxia", Cancer Res., Nov. 15, 2016, vol. 76, No. 22, pp. 6643-6656.
Abramson MD, Steven B., "Osteoarthritis and nitric oxide", Osteoarthritis and Cartilage, 2008, vol. 16, Supplement 2, pp. S15-S20.
Alarifi, Saud et al., "Oxidative Stress-Induced DNA Damage by Manganese Dioxide Nanoparticles in Human Neuronal Cells", BioMed Research International, vol. 2017, Article ID5478790, 10 pages.
Bajpayee, Ambika G. et al., "Avidin as a model for charge driven transport into cartilage and drug delivery for treating early stage post-traumatic osteoarthritis", Biomaterials, 2014, vol. 35, pp. 538-549.
Bijlsma, Johannes W. et al., "Osteoarthritis: an update with relevance for clinical practice", Lancet, Jun. 18, 2011, vol. 377, pp. 2115-2126.
Bizeau, Joëlle et al., "Synthesis and characterization of hyaluronic acid coated manganesedioxide microparticles that act as ROS scavengers", Colloids and Surfaces B: Biointerfaces, Mar. 2, 2017, vol. 159, pp. 30-38.
Bohorquez, Ana C. et al., "In Situ Evaluation of Nanoparticle-Protein Interactions by Dynamic Magnetic Susceptibility Measurements", Part. Part. Syst. Charact., 2014, vol. 31, pp. 561-570.
Bottini PhD, Massimo et al., Nanodrugs to target articular cartilage: An emerging platform for osteoarthritis therapy, Nanomedicine: Nanotechnology, Biology, and Medicine, 2016, vol. 12, pp. 255-268.
Broughton D.B. et al., "Mechanism of Decomposition of Hydrogen Peroxide Solutions with Manganese Dioxide. I", Decomposition of Hydrogen Peroxide Solutions with Manganese Dioxide, Apr. 1947, vol. 69, pp. 741-744.
Brown, Shannon et al., "Nanoparticle Properties for Delivery to Cartilage: The Implications of Disease State, Synovial Fluid, and Off-Target Uptake", Mol. Pharmaceutics, 2019, vol. 16, pp. 469-479.
Buckwalter, Joseph A. et al., "The Roles of Mechanical Stresses in the Pathogenesis of Osteoarthritis: Implications for Treatment of Joint Injuries", Cartilage, 2013 vol. 4, No. 4, pp. 286-294.
Canter, P.H. et al., "The antioxidant vitamins A, C, E and selenium in the treatment of arthritis: a systematic review of randomized clinical trials", Rheumatology, 2007, vol. 46, pp. 1223-1233.
Canton, Johnathan et al., "Contrasting phagosome pH regulation and maturation in human M1 and M2 macrophages", Molecular Biology of the Cell, Nov. 1, 2014, vol. 25, pp. 3330-3341.
Casbon, Amy-Jo et al., "Effects of IFN-γ on intracellular trafficking and activity of macrophage NADPH oxidase flavocytochrome b558" Journal of Leukocyte Biology, Oct. 2012, vol. 92, pp. 869-882.
Cassatella, Marco A. et al., "Molecular Basis of Interferon-γ and Lipopolysaccharide Enhancement of Phagocyte Respiratory Burst Capability", The Journal of Biological Chemistry, Nov. 25, 1990, vol. 265, No. 33, pp. 20241-20246.
Collins, John A. et al., "Targeting aging for disease modification in osteoarthritis", Curr Opin Rheumatol, Jan. 2018, vol. 30, No. 1, pp. 101-107.
Covarrubias, Anthony et al., "ROS sets the stage for macrophage differentiation", Cell Research, 2013, vol. 23, pp. 984-985.
Croft, Andrew J. et al., "Macrophage Polarization Alters Postphagocytosis Survivability of the Commensal Streptococcus gordonii", Infection and Immunity, Mar. 2018, vol. 86 Issue 3, e00858-17, 14 pages.
Daheshia Dr. M. et al., "The Interleukin 1β Pathway in the Pathogenesis of Osteoarthritis", The Journal of Rheumatology, 2008, vol. 35, No. 12, pp. 2306-2312.
Dey, Swati et al., "Compartment-specific Control of Reactive Oxygen Species Scavenging by Antioxidant Pathway Enzymes", The Journal of Biological Chemistry, May 20, 2016, vol. 291, No. 21, pp. 11185-11197.
Eichaker, Lauren R. et al., "Future nanomedicine for the diagnosis and treatment of osteoarthritis", Nanomedicine (Lond.), 2014, vol. 9, No. 14, pp. 2203-2215.
Evans, Christopher H. et al., "Progress in intra-articular therapy", Nat. Rev. Rheumatol, Jan. 2014, vol. 10, pp. 11-22.
Fan, Huanhuan et al., "A Smart Photosensitizer—Manganese Dioxide Nanosystem for Enhanced Photodynamic Therapy by Reducing Glutathione Levels in Cancer Cells", Angew. Chem., 2016, vol. 128, pp. 5567-5572.
Forman, Henry Jay et al., "Redox signaling in macrophages", Molecular Aspects of Medicine, 2001, vol. 22, pp. 189-216.
Gerwin, N. et al., "The OARSI histopathology initiative e recommendations for histological assessments of osteoarthrtis in the rat", Osteoarthritis and Cartilage, 2010, vol. 18, pp. S24-S34.
Gordijo, Claudia R. et al., "Correction to Multifunctional Albumin-MnO2Nanoparticles Modulate Solid Tumor Microenvironment by Hypoxia, Acidosis, Vascular Endothelial Growth Factor and Enhance Radiation Response", ACS Nano, 2014, vol. 8, pp. 3202-3212.
Greenwald, Robert A., "Therapeutic Benefits of Oxygen Radical Scavenger Treatments Remain Unproven", Journal of Free Radicals in Biology & Medicine, 1985, vol. 1, pp. 173-177.

(56) References Cited

OTHER PUBLICATIONS

Greenwald, Robert A., "Oxygen Radicals, Inflammation, and Arthritis: Pathophysiological Consideration and Implications for Treatment", Seminars in Arthritis and Rheumatism, Feb. 1991, vol. 20, No. 4, pp. 219-240.

Grover, Ashok Kumar et al., "Benefits of antioxidant supplements for knee osteoarthritis: rationale and reality", Nutrition Journal, 2016, vol. 15, No. 1, 13 pages.

Han, Derick et al., "Voltage-dependent Anion Channels Control the Release of the Superoxide Anion from Mitochondria to Cytosol", The Journal of Biological Chemistry,Feb. 21, 2003, vol. 278, No. 8, pp. 5557-5563.

Hiran, Tejindervir S. et al., "Detection of Superoxide and NADPH Oxidase in Porcine Articular Chondrocytes", Free Radical Biology & Medicine, 1997, vol. 23, No. 5, pp. 736-743.

Holyoak, Derek T. et al., "Osteoarthritis: Pathology, mouse models, and nanoparticle injectable systems for targeted treatment", Ann Biomed Eng., Jun. 2016, vol. 44, No. 6, pp. 2062-2075.

Hootman, Jennifer M. et al., "Projections of US Prevalence of Arthritis and Associated Activity Limitations", Arthritis & Rheumatism, Jan. 2006, vol. 54, No. 1, pp. 226-229.

Howard, Kenneth A. et al., "Chitosan/siRNA Nanoparticle-mediated TNF-α Knockdown in Peritoneal Macrophages for Anti-inflammatory Treatment in a Murine Arthritis Model", Molecular Therapy, Jan. 2009, vol. 17, No. 1, pp. 162-168.

Kavanaugh, Taylor E. et al., "Particle Based Technologies for Osteoarthritis Detection and Therapy", Drug Deliv Transl Res, Apr. 2016, vol. 6, No. 2, pp. 132-147.

Kloefkorn, H.E. et al., "A graphic user interface for the evaluation of knee osteoarthritis (GEKO): an open-source tool for histological grading", Osteoarthritis and Cartilage, 2019, vol. 27, pp. 114-117.

Kumar, Shreedevi et al., "Manganese dioxide nanoparticles protect cartilage from inflammationinduced oxidative stress", Biomaterials, 2019, vol. 224, No. 119467, 20 pages.

Lawrence, Reva C. et al., "Estimates of the Prevalence of Arthritis and Other Rheumatic Conditions in the United States", Arthritis & Rheumatism, Jan. 2008, vol. 58, No. 1, pp. 26-35.

Lepetsos, Panagiotis et al., "ROS/oxidative stress signaling in osteoarthritis", Biochimica et Biophysica Acta, 2016, vol. 1862, pp. 576-591.

Levick, J.R., "Flow tThrough Interstitium and Other Fibrous Matrices", Quarterly Journal of Experimental Physiology, 1987, vol. 72, pp. 409-438.

Loeser, Richard F., "Aging processes and the development of osteoarthritis", Curr Opin Rheumatol, Jan. 2013, vol. 25, No. 1, pp. 108-113.

Loeser, Richard F. et al., "Ageing and the pathogenesis of osteoarthritis",Nature Reviews Rheumatology,Jul. 2016, vol. 12, pp. 412-420.

Luo, Yonglan, "Preparation of MnO2 nanoparticles by directly mixing potassium permanganate and polyelectrolyte aqueous solutions", Materials Letters, 2007, vol. 61, pp. 1893-1895.

Moulton, P.J. et al, "Detection of Protein and mRNA of Various Components of the NADPH Oxidase Complex in an Immortalized Human Chondrocyte Line", British Journal of Rheumatology, 1997, vol. 36, pp. 522-529.

Mwangi, Timothy K. et al., "Synthesis and characterization of silk fibroin microparticles for intra-articular drug delivery", International Journal of Pharmaceutics, 2015, vol. 485, pp. 7-14.

Newburger, Peter E. et al., "In Vitro Regulation of Human Phagocyte Cytochrome b Heavy and Light Chain Gene Expression byBacterial Lipopolysaccharide and Recombinant Human Cytokines", The Journal of Biological Chemistry, Aug. 25, 1991, vol. 266, No. 24, pp. 16171-16177.

Prasad Preethy et al., "Multifunctional AlbuminMnO2Nanoparticles Modulate Solid Tumor Microenvironment by Attenuating Hypoxia, Acidosis, Vascular Endothelial Growth Factor and Enhance Radiation Response", American Chemical Society, 2014, vol. 8, No. 4, pp. 3202-3212.

Regan, Elizabeth et al., "Extracellular Superoxide Dismutase and Oxidant Damage in Osteoarthritis", Arthritis & Rheumatism, Nov. 2005, vol. 52, No. 11, pp. 3479-3491.

Roach, Helmtrud I., "The Complex Pathology of Osteoarthritis: Even Mitochondria Are Involved", Arthritis & Rheumatism, Aug. 2008, vol. 58, No. 8, pp. 2217-2218.

* cited by examiner

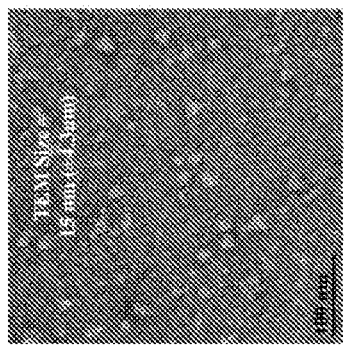
FIG. 1C
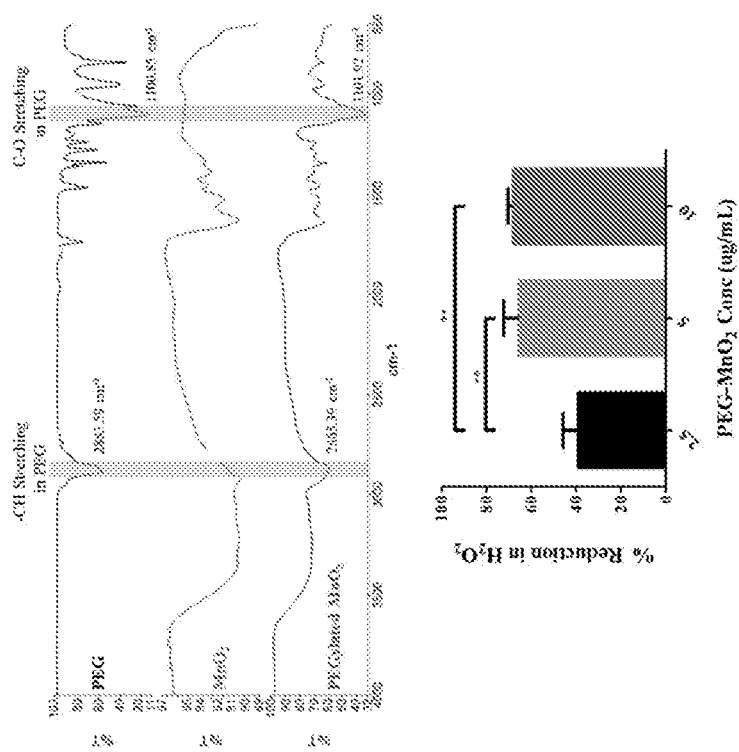
FIG. 1D
FIG. 1E

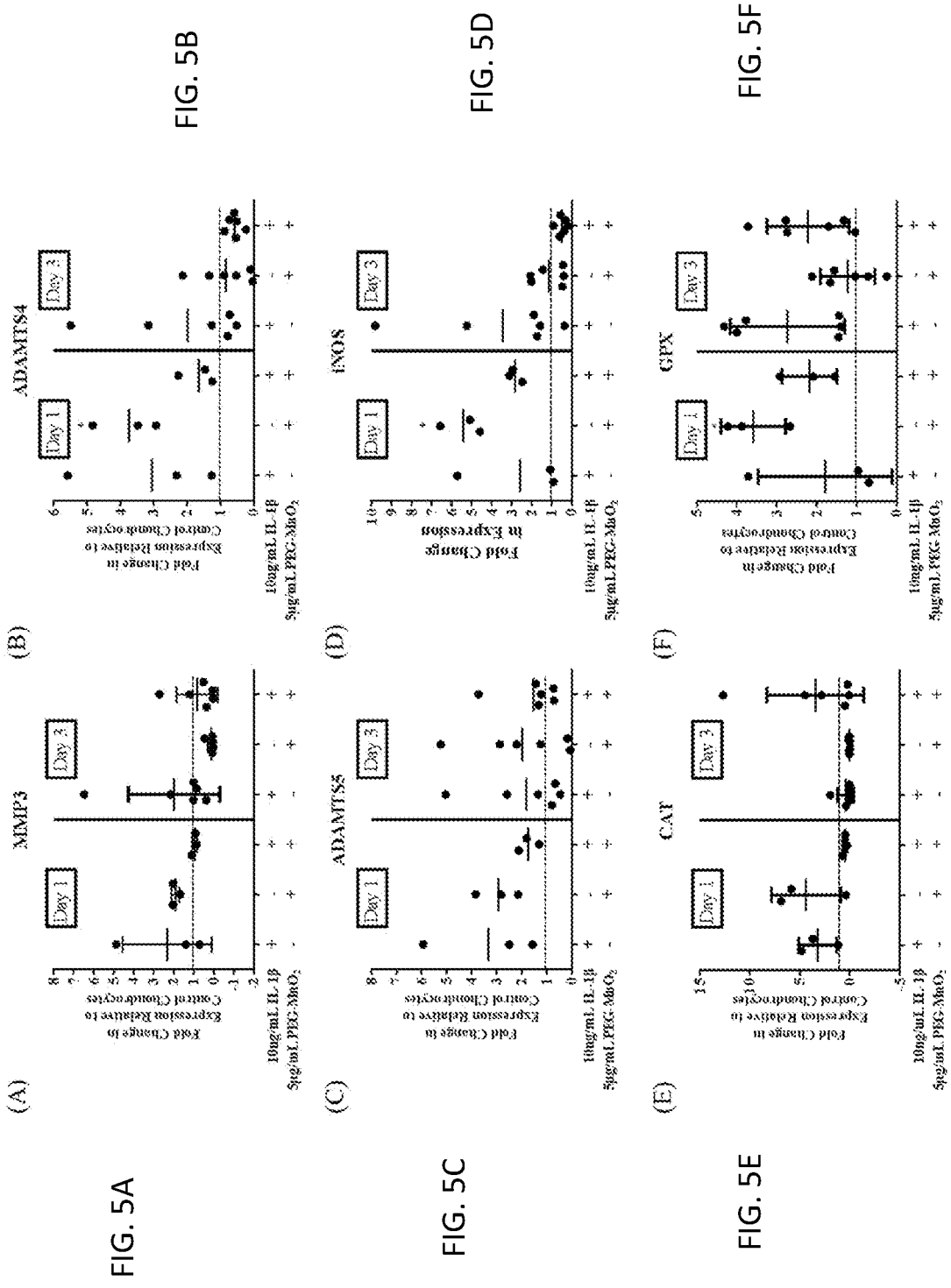

COMPOSITION AND METHOD FOR TREATING OSTEOARTHRITIS WITH MANGANESE DIOXIDE NANOPARTICLES

STATEMENT OF GOVERNMENT INTEREST

This invention was made with government support under R01 AR071335 awarded by The National Institute of Health. The government has certain rights in the invention.

This invention was made whole or in part from funds received from the Florida Department of Health BioMedical Research Program.

FIELD

The invention relates to the field of bioactive nanoparticles (NPs) that can scavenge reactive oxygen species to decrease oxidative stress, and methods of using these nanoparticles to treat medical conditions in which reactive oxidative species are a cause or a means of producing symptoms. The nanoparticles contain stabilized manganese dioxide with a weighted size of 60 nm (about 15 nm size by transmission electron microscopy) and a zeta potential of about +20 mV to about +40 mV.

BACKGROUND

Osteoarthritis (OA) is a wear-and-tear disease with a multi-factorial etiology that impacts over 30 million Americans, and is the leading cause of activity limitation and absenteeism among working class adults in the United States. This joint disease is characterized by breakdown of joint cartilage and underlying bone. The disease is accompanied by joint pain and stiffness, joint swelling, and decreased range of motion. Osteoarthritis is thought to be caused by mechanical stress on the joint and low grade inflammatory processes whereby oxidative stress contributes to the symptoms.

Treatment currently consists of exercise and pain medications, including anti-inflammatory drugs such as NSAIDS (e.g., naproxen, ibuprofen) and, where available, joint replacement surgery, which lasts about 10-15 years on average. Hyaluronan also sometimes is injected directly into the knee joint, where it is believed to help supplement the knee joint's natural synovial fluid, acting as a lubricant relieving pain and improving your ability to use the knee.

These treatments are not ideal and do not cure the condition. Surgery is not available for all joints and requires considerable recovery time as well as expense. Long-term NSAID therapy also can produce unwanted side effects. Hyaluronan injections must be repeated weekly or at least every several months, and are not always successful. Therefore, there is a need in the art for additional treatments for osteoarthritis.

In addition, there is a need in the art for reduction of oxidative stress generally, because this condition is a causative factor in so many disease conditions. In the case of osteoarthritis, oxidative stress plays a central role in disease pathogenesis including chondrocyte death, senescence, extracellular matrix degradation, and synovial inflammation.

SUMMARY

The nanoparticles disclosed herein are non-toxic to chondrocytes and scavenge reactive oxidative species (hydrogen peroxide) to reduce oxidative stress on tissues such as cartilage, in order to modulate joint pain and inflammation. The manganese dioxide nanoparticles protect cartilage from interleukin-1β-induced glycosaminoglycan loss and production of nitric oxide.

In summary, the nanoparticles effectively scavenged $H_2O_2$, with 5 μg/mL manganese dioxide nanoparticles neutralizing 55% of 100 μM $H_2O_2$. Chondrocytes in monolayer showed uptake of the manganese dioxide nanoparticles without cytotoxicity. In ex vivo cartilage explants, the nanoparticles penetrated through the depth of the biopsies and were retained within the tissue matrix. In cytokine-challenged cartilage explants, supplementation with manganese dioxide nanoparticles decreased nitric oxide production by 80% ($p<0.0001$) and reduced glycosaminoglycan loss by 55% ($p<0.01$) compared to controls. After in vivo injection in rat articular joints, Alexa 750 labelled manganese dioxide nanoparticles displayed a linear decline ($R2=0.95$) in fluorescent signal with time with 63% of the initial amount of nanoparticles remaining in joints 11 days post-injection. Given their joint retention time and ROS scavenging capacity, these nanoparticles were found to target oxidative stress mechanisms suitably to treat or prevent osteoarthritis.

Therefore, certain embodiments relate to a method of treating osteoarthritis in the joint of a subject in need thereof, comprising injecting the joint intra-articularly with a manganese dioxide nanoparticle formulation, wherein the manganese dioxide nanoparticle formulation comprises:

(a) a plurality of manganese dioxide nanoparticles having a size by transmission electron microscopy of about 5 to about 30 nm;

(b) a stabilizer comprising succinimidyl valerate poly (ethylene glycol); and (c) an aqueous pharmaceutically acceptable carrier for injection.

In specific methods, the manganese dioxide nanoparticle formulation inhibits glycosaminoglycan loss in cartilage in the joint and/or the manganese dioxide nanoparticle formulation reduces nitric oxide in cartilage in the joint.

In addition, in some embodiments, the manganese dioxide nanoparticles are administered to address a tissue defect. The tissue defect site is at least partially located in an inner or avascular region of a cartilaginous tissue. In some embodiments, the tissue defect includes a tear, injury, or degeneration, as well as osteoarthritis as described herein. In some embodiments, the tissue defect includes a longitudinal or vertical tear, a radial tear, a horizontal tear, a bucket handle tear, a parrot beak tear, or a flap tear. In some embodiments, the tissue (in which the defect is present) can be cartilaginous tissue, cartilage, a meniscus, a knee meniscus, a ligament, a ligament enthesis, a tendon, a tendon enthesis, an intervertebral disc, a temporomandibular joint (TMJ), a TMJ ligament, or a triangular fibrocartilage. Features related to tissue and tissue defect can be combined with other features discussed above and below.

In addition, certain embodiments relate to manganese dioxide nanoparticles that are able to catalyze the breakdown of $H_2O_2$ in inflammatory diseases. In particular, exemplary embodiments are directed to a manganese dioxide nanoparticle, which is produced by (a) adding poly(allylamine hydrochloride) and KMnO4 in a 1:1 ratio to water with mixing; (b) washing the nanoparticles formed and suspending the nanoparticles in water; (c) adding succinimidyl valerate poly(ethylene glycol) to the nanoparticles, with further mixing; and (d) washing the nanoparticles. These particles preferably have a size of about 5 nm to about 30 nm by transmission electron microscopy or a size of about 15 nm to about 200 nm by dynamic light scattering and most preferably have a size of about 15 nm by transmission electron microscopy or a size of about 67 nm by dynamic light scattering.

Also disclosed is a manganese dioxide nanoparticle formulation, comprising the manganese dioxide nanoparticle(s) as described and a pharmaceutically acceptable carrier. For example, a specific embodiment pertains to a manganese dioxide nanoparticle formulation, comprising (a) a plurality of manganese dioxide nanoparticles having a size by transmission electron microscopy of about 5-30 nm; (b) a stabilizer comprising succinimidyl valerate poly(ethylene glycol); and (c) an aqueous pharmaceutically acceptable carrier.

The disclosure also relates to a method of treating oxidative stress in a subject in need thereof, comprising administering to the subject the manganese dioxide nanoparticle(s) as described here, and a method of treating oxidative stress in a subject in need thereof, comprising administering to the subject the manganese dioxide nanoparticle formulation(s) as described here. The subject can be a mammal, preferably a human. The subject can suffer from osteoarthritis. Treatments disclosed herein can be by any convenient route of administration, but preferably is by intra-articular injection.

Certain embodiments also relate to a method of scavenging reactive oxygen species in a tissue, comprising contacting the tissue with the manganese dioxide nanoparticle(s) as described here and to methods of treating osteoarthritis in a subject in need thereof, comprising administering to the subject the manganese dioxide nanoparticle(s) or nanoparticle formulation(s) as described.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIGS. 1A-1E Characterization of PEG-$MnO_2$ NPs. FIG. 1A—PEGylation of the $MnO_2$ NPs prevents them from aggregating in both PBS and synovial fluid. FIG. 1B—In PBS, plain $MnO_2$ NPs were 11.21 nm (number weighted) and +52.12 mV, PEG-$MnO_2$ NPs were 10.92 nm (number weighted) and +26.84 mV and Alexa750 labelled PEG-$MnO_2$ NPs were 10.83 nm (number weighted) and +28.01 mV when measured by DLS where $p≤0.01$ and $p≤0.0001$. FIG. 1C—The TEM size of the PEG-$MnO_2$ NPs was 15.0 nm. FIG. 1D—PEGylation of the $MnO_2$ NPs was confirmed by FTIR. FIG. 1E—The PEG-$MnO_2$ NPs were effective in scavenging $H_2O_2$, with 5 ug/mL $MnO_2$ NPs neutralizing 65% of 100 uM $H_2O_2$ in PBS where $p<0.01$.

FIG. 2A-Primary bovine chondrocytes in monolayer showed uptake of fluorescently tagged PEG-$MnO_2$ NPs which escaped endosomes and localized perinuclearly. FIG. 2B—PEG-$MnO_2$ NPs were not cytotoxic to primary bovine chondrocytes up to a concentration of 100 ug/mL. FIG. 2C—PEG-MnO2 NPs were not cytotoxic to bovine synoviocytes and human MSCs. FIG. 2D—NPs appear to be cytotoxic to inactivated macrophages at concentrations equal to and greater than 20 ug/mL and to classically activated macrophages at concentrations equal to and greater than 1 ug/mL. $p≤0.01$, *$p≤0.001$, ****$p≤0.0001$ relative to the 0 ug/mL PEG-$MnO_2$ for each cell type.

FIG. 3A-250 µg/mL fluorescently tagged PEG-$MnO_2$ NPs penetrated through the depth of the cartilage biopsies and were endocytosed by resident chondrocytes. FIG. 3B—Following 24 hrs of exposure to 5 µg/mL PEG-$MnO_2$ NPs, there was not a significant change in cell viability within experimental explants from control explants by LIVE/DEAD staining or by TUNEL Assay (FIG. 3C). FIG. 3D—24 hrs of exposure to 5 µg/mL PEG-$MnO_2$ NPs did not cause significant changes in extracellular matrix by Safranin-O staining.

FIG. 4C—PEG-$MnO_2$ NPs significantly decreased cumulative glycosaminoglycan (GAG) loss by 50% for cytokine-challenged bovine cartilage explants by day 14. FIG. 4D—This was confirmed by the increasing staining of ECM components by Safranin-O in the cytokine challenged explants exposed to PEG-$MnO_2$ when compared to just the cytokine-challenged explants. FIG. 4E—PEG-$MnO_2$ NPs significantly decreased cumulative nitric oxide (NO) production by 40% for cytokine-challenged bovine cartilage explants by day 14. *$p≤0.05$, $p≤0.01$, *$p≤0.001$, ****$p≤0.0001$ relative to IL-1β and ⊤$p≤0.05$, ⊤⊤$p≤0.01$ relative to PEG-$MnO_2$+IL-1β at each respective timepoint FIGS. 5A-5I. Impact of PEG-$MnO_2$ NPs on gene expression profiles of cytokine-challenged primary bovine chondrocytes. PEG-$MnO_2$ NPs decreased expression of catabolic mediators including matrix metalloproteinase 3 (MMP3) (FIG. 5A), a disintegrin and metalloproteinase with thrombospondin motifs 4 and 5 (ADAMTS4 and ADAMTS5) (FIG. 5B and FIG. 5C) and inducible nitric oxide synthase (iNOS)(FIG. 5D), of anti-oxidants including catalase (CAT) (FIG. E), glutathione peroxidase (GPX) (FIG. 5F) and manganese superoxide dismutase (MnSOD) (FIG. 5G) and of anti-oxidant regulators such as nuclear factor-like 2 (NRF2) (FIG. 5H) and kelch-like ECH-associated protein 1 (KEAP1) (FIG. 5I) by cytokine-challenged chondrocytes.

FIG. 6B—In a separate cohort of animals, a biodistribution study revealed nanoparticle accumulation within the extensor mechanism and chondral surfaces (patella, femoral condyles, and tibial plateau) at the end of a 11-day study. FIG. 6C—The Alexa Fluor 594 labelled PEG-$MnO_2$ NPs within knee joint 2 days post-injection in a histological sample was distributed in the chondral surfaces. FIG. 6D—NPs displayed minimal accumulation in key organs 11 days post-injection. FIG. 6E—Representative histological images of toluidine stained knee sections and representative parameter of evaluation of knee OA using GEKO software. Non-significant differences were found between the groups for cartilage matrix loss width 0%, 50% and 100% lesion depth, total cartilage degeneration width, significant cartilage degeneration width, zone 1, 2 and 3 depth ratio of lesion and osteophyte size. This evaluation revealed minimal long-term cytocompatibility of the particles.

FIG. 7 Scheme 1. Experimental plan for in vitro study of the therapeutic impact of PEG-$MnO_2$ on bovine cartilage explants. Fresh 4 mm diameter bovine cartilage explants were incubated in chondrocyte media over a 14-day period and challenged with 10 ng/mL human recombinant IL-1β in the presence and absence of 5 ug/mL PEG-MnO$_2$ NPs. The media was changed every 2-3 days. While the IL-1β was added with every media change for groups exposed to IL-1β, the PEG-MnO$_2$ was only added on Day 0 and 7 for the relevant groups.

FIG. 8 Scheme 2. Experimental plan for in vitro study of the impact of PEG-MnO$_2$ on gene expression of bovine chondrocytes. Primary bovine chondrocytes were challenged with 10 ng/mL human recombinant IL-1β in the presence and absence of 5 μg/mL PEG-MnO$_2$ NPs. Primary bovine chondrocytes were serum starved for 24 hours in low-serum chondrocyte media (1% FBS) before being challenged with 10 ng/mL human recombinant IL-1β in the presence and absence of 5 μg/mL PEG-MnO$_2$ NPs in Earle's Balanced Salt Solution (EBSS) for 24 hours. RNA was extracted from Day 1 samples (n=3 per group) while the treatments were removed from Day 3 samples and fresh chondrocyte media was added to them. RNA was extracted from Day 3 samples (n=6 per group) after 48 hours of incubation in the media.

DETAILED DESCRIPTION

Figure 1A:
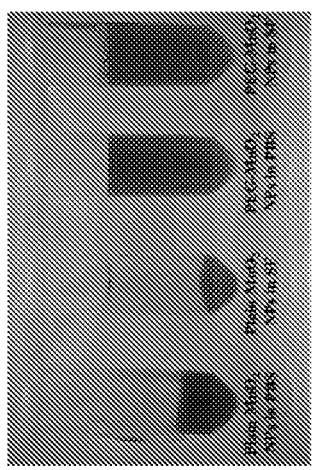

In this disclosure, it is shown that MnO$_2$ nanoparticles (NPs) will protect cartilage from inflammation-induced oxidative stress in both an in vitro cytokine-challenged cartilage system and an in vivo animal model of PTOA. Use of engineered small (less than 15 nm), cationic MnO$_2$ NPs facilitated uptake and penetration through cartilage and increased their chondroprotective capacity. Based on this discovery, embodiments of the invention include the use and administration of NPs to treat or prevent osteoarthritis, and to accelerate healing of articular cartilage tissues.

Manganese dioxide nanoparticles can reduce oxidative stress in osteoarthritic cartilage. Given their joint retention time and ROS scavenging capacity, these nanoparticles can target oxidative stress to treat or prevent osteoarthritis. Since the nanoparticles show intracellular localization in chondrocytes, they also can deliver other chondroprotective agents including nucleic acids to target multiple pathways in the osteoarthritis pathology.

The manganese dioxide nanoparticles disclosed herein are formulated in a pharmaceutically acceptable carrier under sterile conditions and injected into a joint. The dosage given is easily ascertainable by the person of skill and will depend upon the size of the joint, the severity of the condition and other physical parameters unique to the patient being treated. The treatment can be administered daily, weekly or monthly, and can be administered one time or as a series of treatments. The treatment can be given in combination with other pharmaceutical agents in one formulation or in separate formulations to be administered by injection to the joint, intravenously or orally.

1. DEFINITIONS

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount. Unless defined otherwise, all technical and scientific terms used herein have the same meaning as commonly understood by one of ordinary skill in the art.

A mammal, as used herein, refers to any of the class Mammalia, including, but not limited to laboratory, farm, or companion animals such as rats, mice, rabbits, bovines, equines, ovines, porcines, canines, felines, simians, humans, and the like.

A nanoparticle or nanoparticles, as used herein, refers to particles having a size from about 1 nm to about 250 nm, preferably about 5 nm to about 100 nm, and more preferably about 5 nm to about 50 nm, unless the size is specifically stated.

A manganese dioxide nanoparticle, as used herein, refers to a nanoparticle comprising manganese dioxide, preferably containing about 33% w/w manganese dioxide to about 66% w/w manganese dioxide, more preferably about 40% w/w manganese dioxide to about 60% w/w manganese dioxide and most preferably about 50% w/w manganese dioxide. Regarding the use of the term "about" with respect to describing composition, size or charge of the nanoparticles, "about" includes the stated value and values up to 15%, 20%, or 25% lesser or greater than the stated value. The manganese dioxide nanoparticles may also be pegylated.

The term "PEG-MNO$_2$" as used herein refers to pegylated manganese dioxide nanoparticle(s).

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication, amelioration or stabilization of the underlying disorder being treated (e.g., in the context of many gastrointestinal diseases, complete or substantially complete mucosal healing). Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "preventing" as used herein refers to administering nanoparticles or nanoparticle compositions for prophylactic benefit to a patient at risk of developing a particular disease (e.g. osteoarthritis), or to a patient reporting one or more of the physiological symptoms of a disease, even though a diagnosis of this disease may not have been made. For example, it is known that certain joint injuries are prone promote osteoarthritis and the nanoparticles can be administered to prevent osteoarthritis in such patients. For purposes of this invention, beneficial or desired clinical results include, but are not limited to, one or more of the following: reducing, decreasing symptoms resulting from the disease, increasing the quality of life of those suffering from the disease, decreasing the dose of other medications required to treat the disease, enhancing the effect of another medication, delaying the progression of the disease, and/or prolonging survival of individuals. Treatment includes preventing the disease, that is, causing the clinical symptoms of the disease not to develop by administration of a protective composition prior to the induction of the disease, suppressing the disease, that is, causing the clinical symptoms of the disease not to develop by administration of a protective composition after the inductive event but prior to the clinical appearance or reappearance of the disease, inhibiting the disease, that is, arresting the development of clinical symptoms by administration of a protective composition after their initial appearance, preventing re-occurring of the disease and/or relieving the disease, that is, causing the regression of clinical symptoms by administration of a protective composition after their initial appearance.

A "therapeutically effective amount" refers to an amount which, when administered in a proper dosing regimen, is sufficient to reduce or ameliorate the severity, duration, or progression of the disorder being treated (e.g., osteoarthritis), prevent the advancement of the disorder being treated (e.g., osteoarthritis), cause the regression of the disorder being treated (e.g., osteoarthritis), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

Reactive oxygen species, as used herein, refers to chemically reactive chemical species containing oxygen, including but not limited to peroxides, superoxide, hydroxyl radical, singlet oxygen, and hydrogen peroxide.

Oxidative stress, as used herein, refers to the systemic manifestation of too high a level of reactive oxygen species in a biological system or animal body, organ or tissue, such that the natural system is not capable of removing or neutralizing the reactive oxygen species or repairing the damage they can cause, resulting in impaired performance of cells.

2. OVERVIEW

Osteoarthritis pathogenesis includes oxidative stress caused by reactive oxygen species (ROS) such as $H_2O_2$. Osteoarthritis is characterized by inflammation in which proinflammatory cytokines, such as IL-1β, upregulate ROS production while downregulating antioxidants in cells. The resulting oxidative stress leads to extracellular matrix degradation, joint inflammation, chondrocyte senescence, and pain. It now has been discovered that manganese dioxide nanoparticles are able to penetrate into cartilage and scavenge for ROS such as $H_2O_2$, protecting tissues from inflammation-mediated oxidative stress and forming the basis for a new treatment for osteoarthritis, as well as other inflammatory diseases such as atherosclerosis. The nanoparticles and formulations of the disclosure, by scavenging for ROS, can reduce the main contributors to joint pain, and also have the ability to decrease glucosaminoglycan (GAG) loss in cartilage, reducing damage, and provide a general decrease in oxidative stress in chondrocytes.

Results described below indicate that the manganese dioxide nanoparticles can reduce oxidative stress in osteoarthritic cartilage. Previous intraarticular therapies often have been inadequate due to rapid clearance of drugs from the joint space with small molecules exiting via the synovial vasculature and larger macromolecules being cleared by the lymphatic system. However, despite the small size of the manganese dioxide nanoparticles used in this study, they were not cleared quickly and instead were retained in the joint space for an extended period of time.

Without wishing to be bound by theory, the small size and positive charge likely enhanced their interactions with the anionic cartilage matrix while facilitating both their penetration through the dense extracellular matrix and endocytosis by resident chondrocytes. This confluence of factors may have enabled their sustained presence in the joint space. The manganese dioxide nanoparticles demonstrated their ability to immediately decompose ROS, as well as provide longer-term protective impacts on cartilage extracellular matrix components and amelioration of reactive nitrogen species. Given their joint retention time and ROS scavenging capacity, these nanoparticles can target oxidative stress mechanisms to treat or prevent osteoarthritis. Because the nanoparticles show intracellular localization in chondrocytes, they could also deliver other chondroprotective agents including nucleic acids to target multiple pathways in osteoarthritis pathology.

Oxidative stress has been implicated in the onset and progression of osteoarthritis (OA), a degenerative disease that impacts over 30 million Americans [1]. OA is the leading cause of activity limitation and absenteeism among working-class adults in the United States and poses a large economic burden [1]. The prevalence of OA is expected to increase, with estimates that by 2030, approximately 25% of the adult population is expected to suffer from OA[2]. There is currently no cure or disease modifying treatment available for this disease and patients are commonly prescribed palliative therapies such as non-steroidal anti-inflammatory drugs (NSAIDS) and analgesics. Promising research has indicated benefits of using anti-oxidants or targeting reactive oxygen species (ROS) mechanisms in the joint to reduce OA severity without having the adverse effects of chronic use of NSAIDs [3,4]. Hence, oxidative stress is a logical therapeutic target for this disease.

Generally, the pathogenesis of OA includes chronic low-grade joint inflammation of the synovial tissues surrounding the joint space. This typically involves the production of pro-inflammatory cytokines such as interleukin-1 (IL-1) by various joint cells leading to autocrine and paracrine interactions with other cells that are stimulated to produce reactive oxygen species (ROS) such as peroxides, hydroxylated radicals, nitric oxide (NO) and downregulate anti-oxidants such as superoxide dismutase (SOD), catalase and glutathione peroxidase [5,6]. The resulting oxidative stress leads to extracellular matrix (ECM) degradation, decreased matrix synthesis, joint inflammation, and chondrocyte death and senescence, thereby contributing to the overall progression of the disease[5].

Although the exact etiology of OA has not been determined, risk factors for the incidence and progression of the disease have been identified and a delineation of the different clinical phenotypes of the disease, including metabolic, ageing-related, post-traumatic, genetic and pain-related OA, have been identified[7]. The presence of oxidative stress is common across the spectrum of OA phenotypes. Aging is a key risk factor OA and several mechanisms are upregulated with aging that could threaten homeostatic balance between ROS and anti-oxidants in the joint[8]. For instance, with mitochondria being a key source of ROS in the cell, chondrocyte mitochondrial dysfunction that occurs with aging has been shown to cause imbalances in ROS production and antioxidant capacities of the cells[9]. Cellular senescence and apoptosis are also prevalent in aged cartilage and are characterized by accumulation of cellular damage, which in turn tend to upregulate ROS in the joint [10]. In post-traumatic osteoarthritis (PTOA), release of ROS occurs from mitochondria in the joint when there is excessive loading on the articular cartilage leading to cartilage cell death and degradation of matrix components[11].

Currently, therapies such as antioxidant supplements, modulation of various ROS pathway mediators and free radical scavengers are being investigated to target the oxidative stress present in OA pathogenesis. Anti-oxidant supplements have had a variable success when used to treat OA. Curcumin, for example, has been shown to inhibit matrix degradation and decrease production of matrix metalloproteinases (MMPs) in vitro, has had bioavailability limitations when delivered either orally or intravenously, limiting therapeutic outcomes in OA patients[3]. Clinical testing of antioxidant vitamins such as Vitamin A, C, E or selenium have either shown contradictory findings or been ineffective in treating arthritis[12,13]. Primary investigations into the upregulation of antioxidant mediators such as heme oxygenase-1 have led decreased expression of MMPs, DNA fragmentation in in vitro systems and reduced severity of OA-like changes in animal models[14,15] but this work has not progressed to the clinical stages yet. Free radical scavengers have also been investigated in osteoarthritis with varying outcomes. In the 1980s, several pharmaceutical companies were involved in conjugating exogenous SOD or catalase to polymers like polyethylene glycol (PEG) or pyran (divinylether maleic acid) to increase half-life and decrease immunogenicity before testing in humans in clinical trials for many diseases including arthritis, pulmonary disease and ischemic tissue damage[16,17]. Orgotein, the drug version of Cu—Zn SOD, has yielded sustained improvements over a six-month period when intra-articularly injected at a high dosage into OA patients as compared to patients who received half the dosage or patients who received injections of a corticosteroid, methylprednisolone acetate[18]. This drug has been used commonly in Europe for the treatment of OA. However, orgotein must be injected at a high dosage and frequency in order to observe effectiveness in treatment. As is evident, many of these therapies that have been developed to target oxidative stress share common limitations including poor bioavailability, poor stability, rapid clearance from the joint and rapid release profiles from various delivery vehicles[19].

Manganese dioxide ($MnO_2$) has been shown to catalyze the breakdown of hydrogen peroxide ($H_2O_2$)[20], a key radical that is derived from superoxide anions ($O_2^-$), one of the main reactive oxidative species produced by chondrocytes[21,22]. $MnO_2$ is currently being evaluated for scavenging ROS in other inflammatory conditions. In an in vitro atherosclerosis model, microparticles comprised of $MnO_2$ core demonstrated continuous scavenging of $H_2O_2$ in an environment mimetic of inflamed tissues[23]. In multiple solid tumor models, $MnO_2$ nanoparticles have been used to modulate hypoxia, leading to inhibited tumor growth and increased cancer cell death[24-26], and simultaneously used to as more biocompatible contrast agent in magnetic resonance imaging (MRI) than gadolinium-based therapies[27, 28]. Manganese oxide particles also demonstrated free radical scavenging and cryoprotection of pancreatic islets of Langerhans in vitro[29]. The use of a bioactive nanoparticle that is made of the scavenging material, $MnO_2$, would eliminate issues of rapid release profiles.

3. EXEMPLARY EMBODIMENTS

Manganese dioxide nanoparticles preferably are produced and formulated in aqueous solution and stabilized with polyethylene glycol succinimidyl valerate. Specific examples of methods for producing the formulations are given in Example 1 below.

Nanoparticles known in the art generally are about 1-100 nm in diameter and can be found in different shapes. The nanoparticles, however, are generally spherical and preferably are about 1 nm to about 250 nm, about 1 nm to about 100 nm, about 5 nm to about 100 nm, about 5 nm to about 50 nm, about 5 nm to about 30 nm. Specific sizes include, but are not limited to about 5 nm, about 8 nm, about 10 nm, about 15 nm, about 20 nm or about 30 nm, and most preferably about 15 nm, as determined by transmission microscopy, or about 15 nm to about 200 nm as determined by dynamic light scattering. Preferably, the TEM and number weighted DLS average size is approximately 15 nm, and the intensity weighted DLS average size is approximately 60 nm.

The particles disclosed herein preferably have a positive zeta potential. In specific embodiments, the nanoparticles have a zeta potential of about +30 mV to about +35 mV when measured in water according to standard procedures as known in the art. Nanoparticles can have a charge of about +15 mV to about +50 mV, preferably about +20 mV to about +40 mV, more preferably about +25 mV to about +35 mV, and most preferably about +25 mV to about +30 mV.

The person of skill is aware that particle sizes referred to herein are average sizes. For example when a particle size is given as 15 nm, the population of particles can have sizes ranging from 1 nm or less, up to 200 nm or more.

When stabilized by PEG, the pegylated nanoparticles possess lower aggregation propensity. However, pegylation changes the characteristics of the nanoparticles slightly. It was observed that pegylation results statistically significant reduction in zeta potential. The size of the nanoparticles changed very little by pegylation. Importantly, pegylation enabled colloidal stability of the manganese nanoparticles in synovial fluid.

Hydrogen peroxide decomposes naturally at a very slow rate. Manganese dioxide in the nanoparticles catalyzes the release of oxygen from hydrogen peroxide according to the reaction:

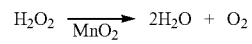

$$H_2O_2 \xrightarrow{MnO_2} 2H_2O + O_2$$

The oxygen escapes as a gas, leaving water, with the reaction proceeding at a much faster rate. The manganese dioxide can act as a catalyst, remaining unchanged, or in some biological systems/contexts will decompose into free manganese ions and oxygen.

The nanoparticles according to the present disclosure preferably are formulated to form a pharmaceutical composition using a pharmaceutically acceptable carrier or excipient for administration to a subject. The terms "pharmaceutically acceptable carrier," "pharmaceutically acceptable excipient," or "pharmaceutically acceptable vehicle" refer to any convenient compound or group of compounds that is not toxic and that does not destroy or significantly diminish the pharmacological activity of the therapeutic agent with which it is formulated. Such pharmaceutically acceptable carriers or vehicles encompass any of the standard pharmaceutically accepted solid, liquid, or gaseous carriers known in the art, such as those discussed in the art and are well known in the art. Any of the compounds and compositions described in "Remington: The Science and Practice of Pharmacy" (20th edition, Gennaro (ed.) and Gennaro, Lippincott, Williams & Wilkins, 2000, are contemplated for use with the compositions of the invention.

Preferably, the disclosed nanoparticles are administered as a composition containing a liquid carrier or vehicle for injection. Any liquid carrier that is compatible with the nanoparticles and the body of the subject to which it is intended to be administered may be used. Preferably, the carrier is aqueous, such as water, distilled water, deionized water, saline, buffered saline (e.g., phosphate buffered saline), Ringer's solution or lactated Ringer's solution, with the formulation taking the form of a solution or suspension. In addition, the formulation can be an oil-in-water or water-in-oil emulsion or the like. The formulation also can be provided as a solid for dilution with a liquid carrier prior to administration.

The pharmaceutically acceptable carrier also can contain additional compounds such as pH adjusters (acid or base), solubilizers, emulsifiers, salts, preservatives, antimicrobial compounds, and the like. Acceptable salts can include, but are not limited to acetate, adipate, alginate, ammonium, aspartate, benzoate, benzenesulfonate (besylate), bicarbonate, bisulfate, butyrate, citrate, camphorate, camphorsulfonate, carbonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, magnesium, maleate, malonate, methanesulfonate (mesylate), 2-naphthalenesulfonate, nicotinate, nitrate, oxalate, palmoate, pectinate, persulfate, 3-phenylpropionate, phosphate, picrate, pivalate, potassium, propionate, salicylate, sodium, succinate, sulfate, tartrate, thiocyanate, toluenesulfonate (tosylate) and undecanoate salts, for example.

Oxidative stress refers to a condition in which reactive oxygen species (usually from oxidative metabolism) exist in amounts too high for the biological system in which they are present to detoxify the reactive oxygen species or the reactive intermediates, or to repair the damage caused by the reactive oxygen species. Most of the damage is caused by superoxide radicals, hydroxyl radicals or hydrogen peroxide. Production of peroxides and free radicals can damage proteins, lipids, and DNA, and disrupt normal cellular mechanisms. The damage is thought to be related to various disease conditions, including cancer, Parkinson's disease, Alzheimer's disease, autism, infection, and others. Reactive oxygen species also are implicated in inflammatory conditions such as osteoarthritis or tissue defect.

The particles according to embodiments of the invention are able to penetrate cartilage tissue, to reduce oxidative stress and also to reduce loss of glycosaminoglycan, which benefits the patient in treatment of osteoarthritis. The manganese dioxide nanoparticles disclosed herein can be used to reduce oxidative stress in any location, but they are advantageously used in the joints for treatment of inflammation and/or osteoarthritis.

Given their ameliorative impact on matrix component (GAG) loss and ROS released by cartilage explants. Manganese dioxide nanoparticles can reduce oxidative stress in cartilage, including in osteoarthritis.

Substrates and Scaffolds

As evident by the exemplary experiments described above, some embodiments include a delivery substrate into which the disclosed nanoparticles are loaded and optionally configured to release the nanoparticles at the site of need. In some embodiments, a release rate can be quantified as a number of days needed to release a majority of or substantially all of the factor from the delivery substrate. A delivery substrate can comprise a matrix material (as defined herein) or be a separate material in or on a matrix material. For example, a delivery substrate can be a matrix material, such as fibrin glue. In some embodiments, the substrate (i.e., matrix material) can be a temporary substrate. For example, a temporary substrate can be hydrogel. The substrate can be suitable for cell migration, tissue formation, delivery of cells, or delivery of biochemical cues (e.g., disclosed nanoparticles). The substrate can be a fibrin gel or a fibrin glue. For example, the substrate can be a higher density fibrin gel or higher density fibrin glue. Higher density fibrin can provide sustained, long-term delivery of nanoparticles.

The substrate can comprise a matrix material having different phases of viscosity. For example, a matrix can have a substantially liquid phase or a substantially gelled phase. The transition between phases can be stimulated by a variety of factors including, but limited to, light, chemical, magnetic, electrical, and mechanical stimulus. For example, the matrix can be a thermosensitive matrix with a substantially liquid phase at about room temperature and a substantially gelled phase at about body temperature. The liquid phase of the matrix can have a lower viscosity that provides for optimal distribution of growth factors or other additives and injectability, while the solid phase of the matrix can have an elevated viscosity that provides for matrix retention at or within the target tissue.

Various embodiments described herein may employ a scaffold loaded with manganese dioxide nanoparticles disclosed herein. The scaffold material can be a biocompatible material that generally forms a porous, microcellular scaffold, which provides a physical support for cells migrating thereto. Such materials can: allow cell attachment or migration; deliver or retain cells or biochemical factors; enable diffusion of cell nutrients or expressed products; or exert certain mechanical or biological influences to modify the behavior of the cell phase. The scaffold material generally forms a porous, microcellular scaffold of a biocompatible material that provides a physical support or an adhesive substrate for recruitment or growth of cells during in vitro or in vivo culturing.

Suitable scaffold or matrix materials are discussed in, for example, Ma and Elisseeff, ed. (2005) Scaffolding In Tissue Engineering, CRC, ISBN 1574445219; Saltzman (2004) Tissue Engineering: Engineering Principles for the Design of Replacement Organs and Tissues, Oxford ISBN 019514130X. For example, matrix materials can be, at least in part, solid xenogenic (e.g., hydroxyapatite) (Kuboki et al. 1995 Connect Tissue Res 32, 219-226; Murata et al. 1998 Int J Oral Maxillofac Surg 27, 391-396), solid alloplastic (polyethylene polymers) materials (Saito and Takaoka 2003 Biomaterials 24 2287-93; Isobe et al. 1999 J Oral Maxillofac Surg 57, 695-8), or gels of autogenous (Sweeney et al. 1995. J Neurosurg 83, 710-715), allogenic (Bax et al. 1999 Calcif Tissue Int 65, 83-89; Viljanen et al. 1997 Int J Oral Maxillofac Surg 26, 389-393), or alloplastic origin (Santos et al. 1998. J Biomed Mater Res 41, 87-94), or combinations of the above (Alpaslan et al. 1996 Br J of Oral Maxillofac Surg 34, 414-418).

The scaffold or substrate can have an adequate porosity and an adequate pore size so as to facilitate cell recruitment and diffusion throughout the whole structure of both cells and nutrients. The scaffold can be biodegradable providing for absorption of the scaffold material by the surrounding tissues, which can eliminate the necessity of a surgical removal. The rate at which degradation occurs can coincide as much as possible with the rate of tissue or organ formation. Thus, while cells are fabricating their own natural structure around themselves, the scaffold can provide structural integrity and eventually break down, leaving the neotissue, newly formed tissue or organ which can assume the mechanical load. The matrix can be an injectable matrix in some configurations.

The scaffold can comprise one or more layers, each with the same or different materials. For example, a scaffold can comprises at least two layers, at least three layers, at least four layers, or more.

The scaffold can comprise a material formed of synthetic polymers. Such synthetic polymers include, but are not limited to, polyurethanes, polyorthoesters, polyvinyl alcohol, polyamides, polycarbonates, polyvinyl pyrrolidone, marine adhesive proteins, cyanoacrylates, analogs, mixtures, combinations or derivatives of the above. Alternatively, the matrix can be formed of naturally occurring biopolymers. Such naturally occurring biopolymers include, but are not limited to, fibrin, fibrinogen, fibronectin, collagen, or other suitable biopolymers. Also, the matrix can be formed from a mixture of naturally occurring biopolymers or synthetic polymers. Another example of a matrix material is an injectable citrate-based mussel-inspired bioadhesive (iCMBA).

The substrate or scaffold can include one or more matrix materials including, but not limited to, a collagen gel, a polyvinyl alcohol sponge, a poly(D,L-lactide-co-glycolide) fiber matrix, a polyglactin fiber, a calcium alginate gel, a polyglycolic acid mesh, polyester (e.g., poly-(L-lactic acid) or a polyanhydride), a polysaccharide (e.g. alginate), polyphosphazene, polyacrylate, or a polyethylene oxide-polypropylene glycol block copolymer. Matrices can be produced from proteins (e.g., extracellular matrix proteins such as fibrin, collagen, fibronectin), polymers (e.g., polyvinylpyrrolidone), or hyaluronic acid. Synthetic polymers can also be used, including bioerodible polymers (e.g., poly (lactide), poly(glycolic acid), poly(lactide-co-glycolide), poly(caprolactone), polycarbonates, polyamides, polyanhydrides, polyamino acids, polyortho esters, polyacetals, polycyanoacrylates), degradable polyurethanes, non-erodible polymers (e.g., polyacrylates, ethylene-vinyl acetate polymers or other acyl substituted cellulose acetates and derivatives thereof), non-erodible polyurethanes, polystyrenes, polyvinyl chloride, polyvinyl fluoride, poly(vinylimidazole), chlorosulphonated polyolifins, polyethylene oxide, polyvinyl alcohol, Teflon®, or nylon.

The scaffold can further comprise any other bioactive molecule, for example an antibiotic or an additional chemotactic growth factor or another osteogenic, dentinogenic, amelogenic, or cementogenic growth factor. In some embodiments, the scaffold is strengthened, through the addition of, e.g., human serum albumin (HSA), hydroxyethyl starch, dextran, or combinations thereof. Suitable concentrations of these compounds for use in the compositions of the application are known to those of skill in the art, or can be readily ascertained without undue experimentation.

The concentration of a compound or a composition in the scaffold can vary with the nature of the compound or composition, its physiological role, or desired therapeutic or diagnostic effect. A therapeutically effective amount is generally a sufficient concentration of therapeutic agent to display the desired effect without undue toxicity. For example, the matrix can include a composition comprising manganese dioxide nanoparticles disclosed herein. The compound can be incorporated into the scaffold or matrix material by any known method. In some embodiments, the compound can be imbedded in a gel, e.g., a collagen gel incorporated into the pores of the scaffold or matrix material or applied as a coating over a portion, a substantial portion, substantially all of, or all of the scaffold or matrix material.

Alternatively, chemical modification methods can be used to covalently link a compound or a composition to a matrix material. The surface functional groups of the matrix can be coupled with reactive functional groups of a compound or a composition to form covalent bonds using coupling agents well known in the art such as aldehyde compounds, carbodiimides, and the like. Additionally, a spacer molecule can be used to gap the surface reactive groups and the reactive groups of the biomolecules to allow more flexibility of such molecules on the surface of the matrix. Other similar methods of attaching biomolecules to the interior or exterior of a matrix will be known to one of skill in the art.

Pores and channels of the scaffold can be engineered to be of various diameters. For example, the pores of the scaffold can have a diameter range from micrometers to millimeters. In some embodiments, the pores of the matrix material include microchannels. Microchannels generally have an average diameter of about 0.1 µm to about 1,000 µm, e.g., about 50 µm to about 500 µm (for example about 100 µm, 150µmτι, about 200µητι, about 250µητι, about 300µητι, about 350µητι, about 400 µm, about 450 µm, about 500 µm, or about 550 µm). One skilled in the art will understand that the distribution of microchannel diameters can have any distribution including a normal distribution or a non-normal distribution. In some embodiments, microchannels are a naturally occurring feature of the matrix material(s). In other embodiments, microchannels are engineered to occur in the matrix materials.

Several methods can be used for fabrication of porous scaffolds, including particulate leaching, gas foaming, electrospinning, freeze drying, foaming of ceramic from slurry, and the formation of polymeric sponge. Other methods can be used for fabrication of porous scaffolds include computer aided design (CAD) and synthesizing the scaffold with a bioplotter (e.g., solid freeform fabrication) (e.g., Bioplotter™, EnvisionTec, Germany).

Biologic drugs that can be added to compositions and methods as described herein can include immunomodulators and other biological response modifiers. A biological response modifier generally encompasses a biomolecule (e.g., peptide, peptide fragment, polysaccharide, lipid, antibody) that is involved in modifying a biological response, such as the immune response or tissue or organ growth and repair, in a manner that enhances a particular desired therapeutic effect, for example, the cytolysis of bacterial cells or the growth of tissue- or organ-specific cells or vascularization. Biologic drugs can also be incorporated directly into the matrix component. Those of skill in the art will know, or can readily ascertain, other substances which can act as suitable non-biologic and biologic drugs.

Compositions described herein can also be modified to incorporate a diagnostic agent, such as a radiopaque agent. The presence of such agents can allow the physician to monitor the progression of wound healing occurring internally. Such compounds include barium sulfate as well as various organic compounds containing iodine. Examples of these latter compounds include iocetamic acid, iodipamide, iodoxamate meglumine, iopanoic acid, as well as diatrizoate derivatives, such as diatrizoate sodium. Other contrast agents that can be utilized in the compositions can be readily ascertained by those of skill in the art and can include, for example, the use of radiolabeled fatty acids or analogs thereof.

The concentration of an agent in the composition can vary with the nature of the compound, its physiological role, or desired therapeutic or diagnostic effect. A therapeutically effective amount is generally a sufficient concentration of therapeutic agent to display the desired effect without undue toxicity. A diagnostically effective amount is generally a concentration of diagnostic agent which is effective in allowing the monitoring of the integration of the tissue graft, while minimizing potential toxicity. In any event, the desired concentration in a particular instance for a particular compound is readily ascertainable by one of skill in the art.

Therapeutic Methods

The manganese dioxide nanoparticles disclosed herein, substrate or scaffold loaded with such nanoparticles can be delivered to a tissue using minimally invasive percutaneous or endoscopic procedures, or in conjunction with open surgeries.

As discussed above, also provided is a process of treating osteoarthritis or damaged or injured cartilaginous tissue in a subject in need thereof, so as to reduce the osteoarthritis or promote healing of the damaged or injured cartilaginous tissue. The manganese dioxide nanoparticles disclosed herein or substrates or scaffolds comprising such nanoparticles can be administered or implanted for treatment of fibrocartilage-related injuries, such as to the knee meniscus, intervertebral discs, temporomandibular joint (TMJ) ligaments, or tendons. For example, the nanoparticles or substrates or scaffolds comprising the disclosed nanoparticles can be administered for reducing inflammation, regeneration or healing of other cartilaginous tissues, including articular cartilage, temporomandibular joint (TMJ) disc, or ligament or tendon enthesis. The strategy can be applied to methods for treating tears reaching the avascular region (e.g., inner third zone) of the meniscus, pre-treatment for injury in the avascular region prior to meniscectomy to reduce the amount of meniscus to be removed, or a preventative treatment for patients at risk of osteoarthritis (OA).

In some embodiments, the present disclosure can provide an approach to healing fibrocartilage-related injuries or osteoarthritis. For example, the present disclosure can provide an approach to healing a tear in fibrocartilage tissue, such as a longitudinal or vertical tear, a radial tear, a horizontal tear, a bucket handle tear, a parrot beak tear, or a flap tear. Exemplary tissue for repair with compositions or methods described herein include, but are not limited to, damaged menisci (e.g., knee menisci), damaged ligaments, damaged tendons, damaged intervertebral discs, temporomandibular joints, or damaged triangular fibrocartilage. Damaged tissue can include defects such as tears, injuries, strain, sprain, pull, osteoarthritis, or degeneration.

In some embodiments, tissue for repair with compositions or methods described herein can include a meniscus. A meniscus is a crescent-shaped fibrocartilaginous structure that can partly divides a joint cavity. In humans, menisci can be present in the knee, wrist, acromioclavicular, sternoclavicular, and temporomandibular joints. In other organisms menisci can be present in other joints. The term 'meniscus' can be used to refer to the cartilage of the knee, either to the lateral or medial meniscus. The lateral or medial meniscus are cartilaginous tissues that provide structural integrity to the knee when it undergoes tension or torsion. The menisci can also be known as "semi-lunar" cartilages—referring to their half-moon, crescent shape.

The menisci of the knee consists of two pads of fibrocartilaginous tissue which serve to disperse friction in the knee joint between the lower leg (tibia) and the thigh (femur). Knee menisci are concave on the top and flat on the bottom, articulating with the tibia. While the ends of the thigh bone and the shin bone have a thin covering of soft hyaline cartilage, the menisci are made of tough fibrocartilage and conform to the surfaces of the bones they rest on. One meniscus rests on the medial tibial plateau; this is the medial meniscus. The other meniscus rests on the lateral tibial plateau; this is the lateral meniscus. Knee menisci are attached to the small depressions (fossae) between the condyles of the tibia (intercondyloid fossa), and towards the center they are unattached and their shape narrows to a thin shelf. The blood flow of the meniscus can be from the periphery (outside) to the central meniscus. Blood flow decreases with age and the central meniscus is avascular by adulthood leading to very poor healing rates.

The menisci can act to disperse the weight of the body and reduce friction during movement. Because the condyles of the femur and tibia meet at one point (which changes during flexion and extension), the menisci spread the load of the body's weight. Without the menisci, the weight of the body could be unevenly applied to the bones in the legs (the femur and tibia). This uneven weight distribution can cause the development of abnormal excessive forces leading to early damage of the knee joint. The menisci can also contribute to the stability of the joint. The menisci can be nourished by small blood vessels but have a large area in the center with no direct blood supply (avascular). This presents a problem when there is an injury to the meniscus, as the avascular areas tend not to heal. Without the essential nutrients supplied by blood vessels, healing cannot take place.

In some embodiments, tissue for repair with compositions or methods described herein can be caused by traumatic injury (often seen in athletes) or degenerative processes, which are the most common tear seen in all ages of patients. Meniscal tears can occur in all age groups. Traumatic tears are most common in active people aged 10-45. Traumatic tears are usually radial or vertical in the meniscus and more likely to produce a moveable fragment that can catch in the knee and therefore require surgical treatment.

In some embodiments, tissue for repair with compositions or methods described herein can be caused by an internally or externally rotated knee in a flexed position, with the foot in a flexed position. It is not uncommon for a meniscal tear to occur along with injuries to the anterior cruciate ligament ACL or the medial collateral ligament MCL—these three problems occurring together are known as the "unhappy triad," which is seen in sports such as football when the player is hit on the outside of the knee. Subjects who experience a meniscal tear usually experience pain and swelling as their primary symptoms. Another common symptom is joint locking, or the inability to completely straighten the joint. This is due to a piece of the torn cartilage preventing the normal functioning of the knee joint.

In some embodiments, tissue for repair with compositions or methods described herein can include "torn cartilage". Torn cartilage can refer to an injury to one of the menisci. There are two general types of meniscus injuries, acute tears that are often the result of trauma or a sports injury and chronic or wear-and-tear type tears. Acute tears have many different shapes (vertical, horizontal, radial, oblique, complex) and sizes. They can be treated with surgical repair depending upon the patient's age as they rarely heal on their own. Chronic tears can be treated symptomatically: physical therapy with or without the addition of injections and antiinflammatory medications. If the tear causes continued pain, swelling, or knee dysfunction, then the tear can be removed or repaired surgically.

In some alternative embodiments, administration can be parenteral, pulmonary, oral, topical, intradermal, intramuscular, intraperitoneal, intravenous, subcutaneous, intranasal, epidural, ophthalmic, buccal, or rectal administration. Such alternative administration would apply to use of the manganese dioxide nanoparticles for reducing inflammation in a subject that does not necessarily involve an articular joint or cartilaginous tissue.

In some embodiments, tissue for repair with compositions or methods described herein can be a degenerative tear. Degenerative tears are most common in people from age 40 upward but can be found at any age, especially with obesity. Degenerative meniscal tears are thought to occur as part of the aging process when the collagen fibers within the meniscus start to break down and lend less support to the structure of the meniscus. Degenerative tears can be horizontal, producing both an upper and a lower segment of the meniscus. These segments do not usually move out of place and can be less likely to produce mechanical symptoms of catching or locking.

In some embodiments, compositions described herein can be administered (e.g., through injection) between intervertebral discs to prevent or treat disc degeneration. As another example, compositions described herein can be administered to prevent or treat arthritis. In some embodiments, the compositions and methods described herein can be used to treat any of the above cartilage-related defects or injuries.

The amount of a composition or formulation described herein that can be combined with a pharmaceutically acceptable carrier to produce a single dosage form can vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions or formulations described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where large therapeutic indices are preferred.

The specific therapeutically effective dose level for any particular subject can depend upon a variety of factors including the injury or disorder being treated and the severity of the injury or disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shama (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions as described herein will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of compositions, formulations, or substrates or scaffold comprising compositions described herein can occur as a single event or over a time course of treatment. For example, a composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for fibrocartilage-related degeneration, osteoarthritis or injury.

Various compositions described herein can be administered simultaneously or sequentially with another agent, such as an antibiotic, an anti-inflammatory, or another agent. For example, a composition including disclosed nanoparticles can be administered simultaneously with another agent, such as an antibiotic or an anti-inflammatory.

4. EXAMPLES

It is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined, otherwise, all technical and scientific terms used herein have the same meanings as commonly understood by one of ordinary skill in the art. Although any methods and materials similar or equivalent to those described herein can be used in the practice or testing of embodiments of the present disclosure, the exemplary methods, devices, and materials are now described. All publications mentioned herein, are incorporated by reference in their entirety. Nothing herein is to be construed as an admission that the invention is not entitled to antedate such disclosure by virtue of prior invention.

Example 1 Synthesis and Characterization of Manganese Dioxide Nanoparticles

Figure 1B:
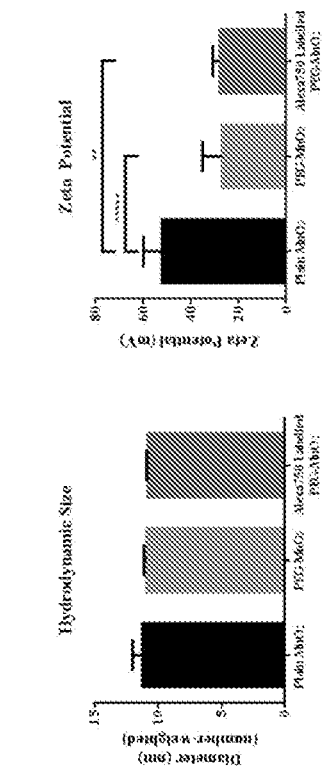

Manganese dioxide ($MnO_2$) NPs were successfully synthesized, with a diameter of 12.85 nm and a zeta potential of +52.12 mV. Bare $MnO_2$ NPs were not colloidally stable in saline or biological fluids such as synovial fluid. Conjugation of PEG to the $MnO_2$ NPs (PEG-$MnO_2$) was required for colloidal stability in saline and synovial fluid (FIG. 1A). Other groups have utilized albumin and hyaluronic acid to stabilize $MnO_2$NPs but this has typically led to a substantial increase in the particle size [25]. In this study, PEGylation maintained the size of the NPs which had a hydrodynamic size of 10.92 nm (number weighted) but decreased the zeta potential of the particles to +29.11 mV (FIG. 1B). Given that the mesh size of the collagen II fibrillar network is ~50-60 nm [34,35] and that there is a ~20 nm spacing[36] between the proteoglycan side chains of cartilage, the maintenance of the small size of particle with PEGylation is critical for their penetration through the dense ECM of cartilage. The size and charge of the NPs did not change significantly when labelled with fluorescence, such as Alexa750. The size of the PEG-$MnO_2$ NPs was confirmed by TEM to be 15 nm (FIG. 1C). The addition of PEG to $MnO_2$ was confirmed using FTIR by the presence of carbon-hydrogen bonds and carbon-oxygen single bonds which are characteristic of PEG (FIG. 1D). The PEG-$MnO_2$ NPs effectively scavenged $H_2O_2$, with 5 ug/mL $MnO_2$ NPs neutralizing 65% of 100 uM $H_2O_2$ (FIG. 1E).

Figure 2A:
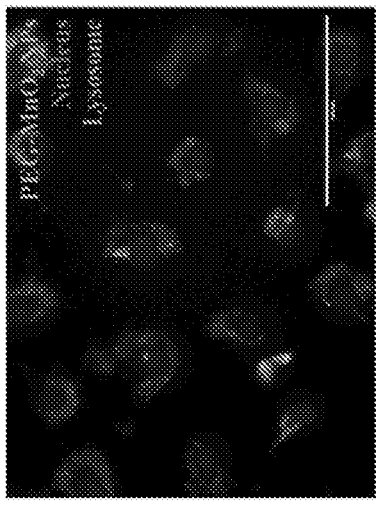
FIGS. 2A-2D Uptake and Cytocompatibility with monolayer of cells.
Figure 2B:
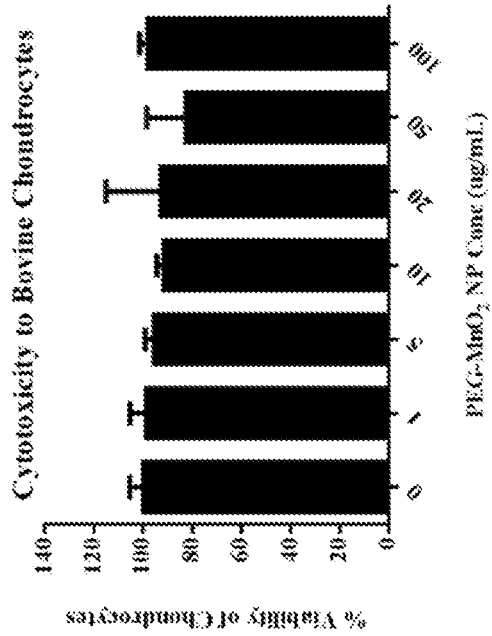

Chondrocytes in monolayer showed uptake of PEG-$MnO_2$ NPs without cytotoxicity. PEG-$MnO_2$ NPs exhibited endosomal escape and localized perinuclearly within the cells (FIG. 2A). As mentioned previously, mitochondria are a vital source of ROS for osteoarthritic chondrocytes. Given that it has been previously demonstrated that the release of ROS from mitochondria to the cytosol occurs via voltage-dependent anion channels [37,38], perinuclear localization of the PEG-$MnO_2$ enables ample opportunity for the NPs to demonstrate their ROS scavenging abilities within the cytosol. The PEG-$MnO_2$ NPs were cytocompatible with chondrocytes in monolayer up to a concentration of 100 μg/mL (FIG. 2B). The NPs were also compatible with some other cells found in the joint space, including synoviocytes and mesenchymal stem cells, and did not impact their proliferation (FIG. 2C).

Figures 2C, 2D:
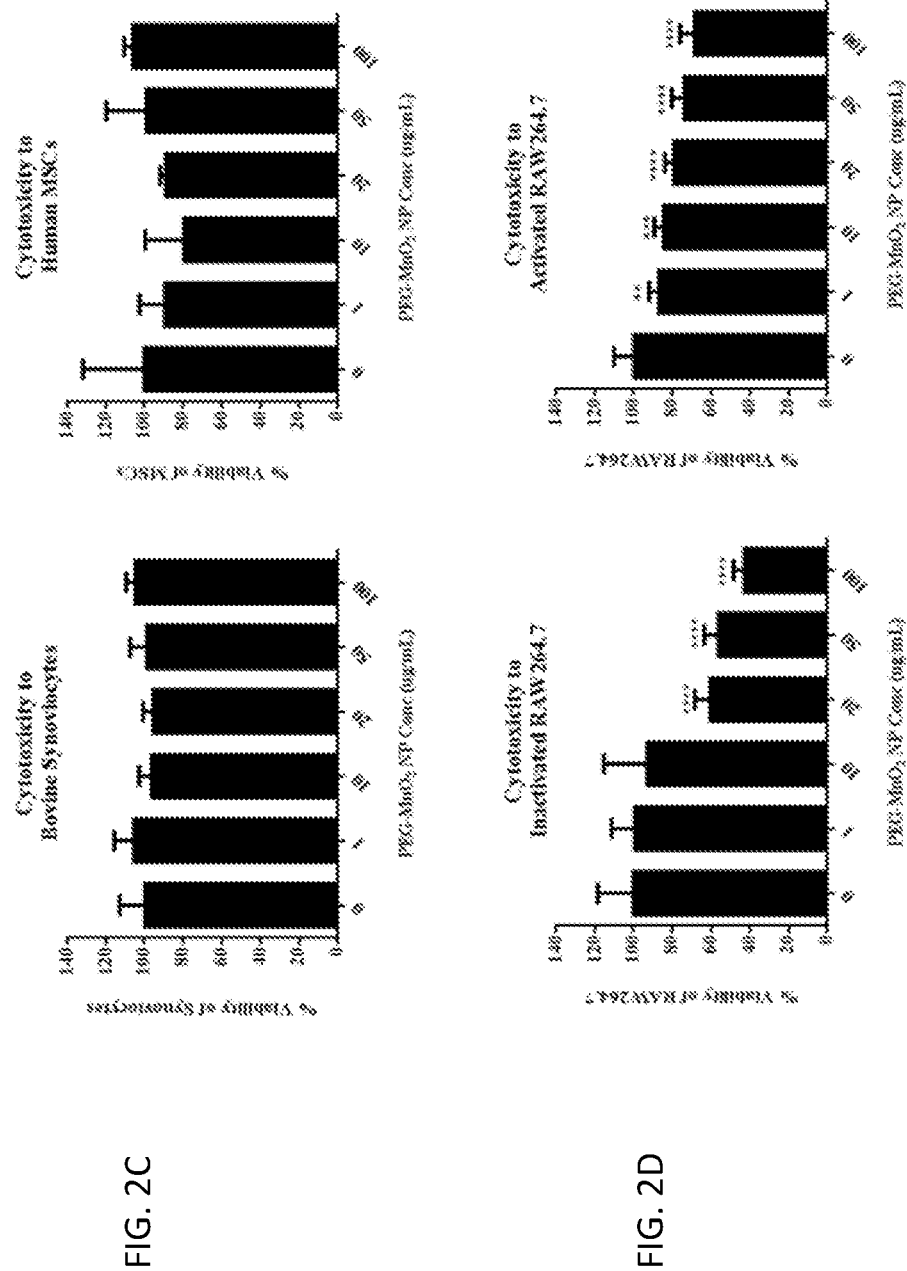

However, the NPs appear to be cytotoxic to inactivated macrophages at concentrations equal to and greater than 20 ug/mL and to classically activated macrophages at concentrations equal to and greater than 1 ug/mL (FIG. 2D). Given that macrophages produce and release ROS in response to phagocytosis or stimulation with various agents[39], it could be expected that the addition of the $MnO_2$ NPs to the cells stimulates greater levels of ROS production by the macrophages than by the other cells in the joint. While ROS are critical inducers of both classical and alternative activation of macrophages[40], an overwhelmed level of intracellular ROS during the differentiation and phagocytosis of macrophages can lead to necrosis of the macrophages[41]. The greater sensitivity of the PEG-$MnO_2$ NPs to the classically activated macrophages could be attributed to the fact that classically activated macrophages are known to have a prolonged phagosomal ROS production compared to alternately polarized macrophages[42]. Specifically, pre-activating macrophages prior to performing assays in an in vitro setting has been shown to increase phagosomal ROS production significantly[43-46]. Hence, the activated macrophages could be experiencing overwhelmed levels of ROS at lower concentrations of PEG-$MnO_2$, leading to death.

Example 2 Protection of Cartilage Tissue by PEG-$MnO_2$ NPs

Figures 3A, 3B:
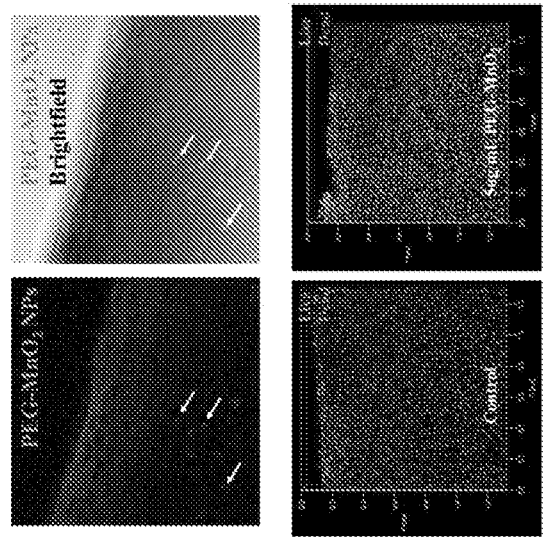
FIGS. 3A-3D Uptake and Cytocompatibility with cartilage explants.
Figures 3C, 3D:
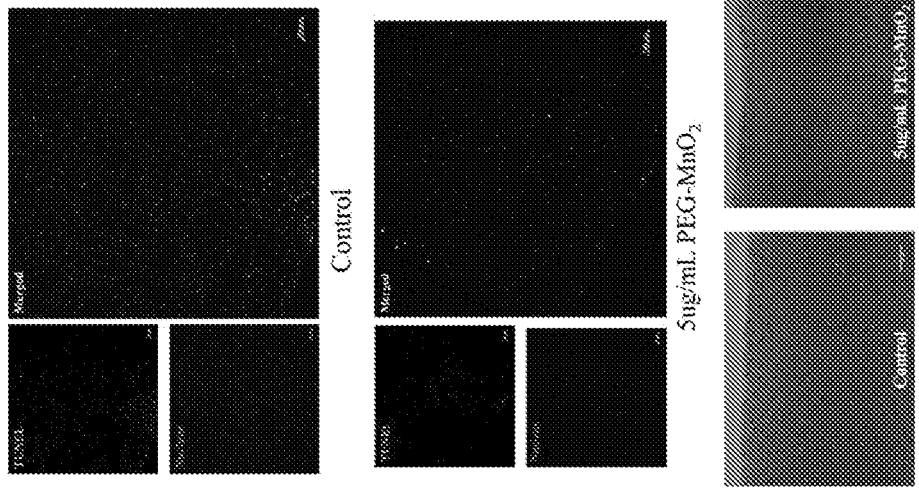

In cartilage explants, fluorescently tagged PEG-$MnO_2$ NPs penetrated through the tissue depth and were retained within the tissue matrix (FIG. 3A). Interestingly, the NPs were also endocytosed by resident chondrocytes following penetration through the matrix. Following 24-hr exposure to 5 ug/mL PEG-$MnO_2$ NPs in chondrocyte media, the cartilage explants did not show significant staining of dead cells by ethidium homodimer-1 (FIG. 3B) or by TUNEL assay (FIG. 3C). The explants also did not exhibit significant changes to extracellular matrix as indicated by Safranin-O staining (FIG. 3D).

Figure 4A:
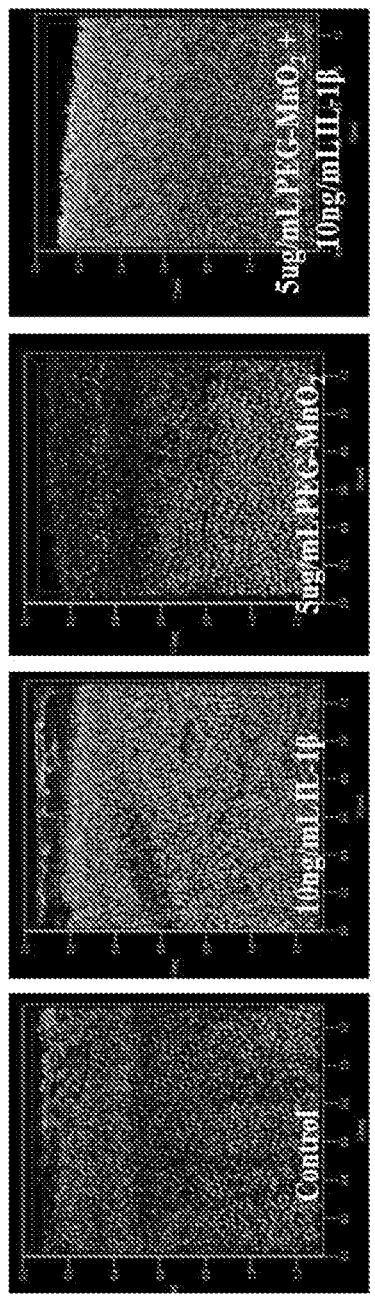
FIGS. 4A-4E. Chondroprotective effects of $MnO_2$ NPs on cytokine challenged cartilage explants. Following 2 weeks of exposure to different combinations of 10 ng/mL IL-1β and/or 5 µg/mL PEG-$MnO_2$ NPs, the bovine cartilage explants exhibited increased viability in the presence of PEG-$MnO_2$ NPs when challenged by IL-1β when measured by LIVE/DEAD Cytotoxicity stain (FIG. 4A) and by TUNEL Assay (FIG. 4B).
Figure 4B:
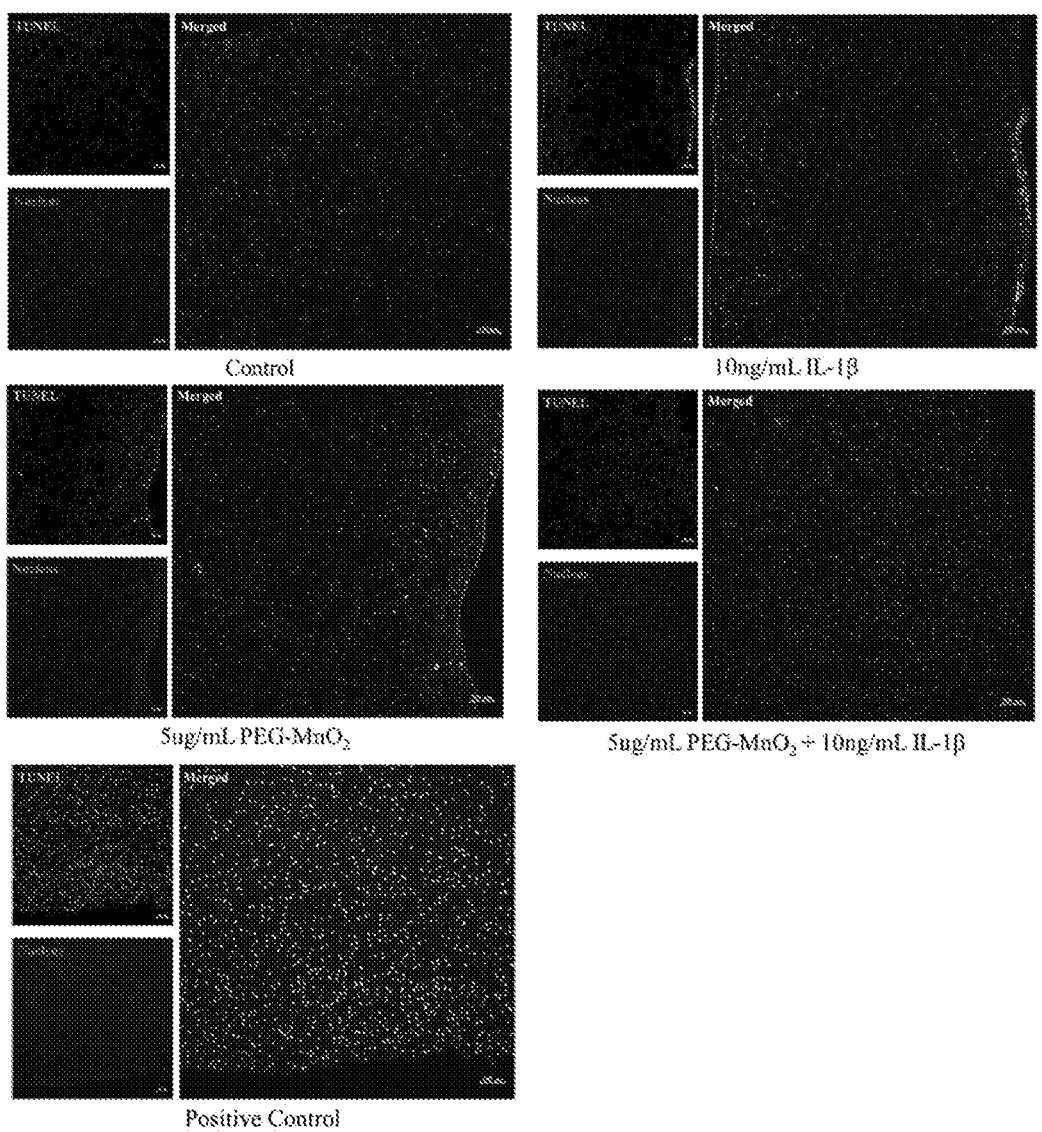
Figure 4C:
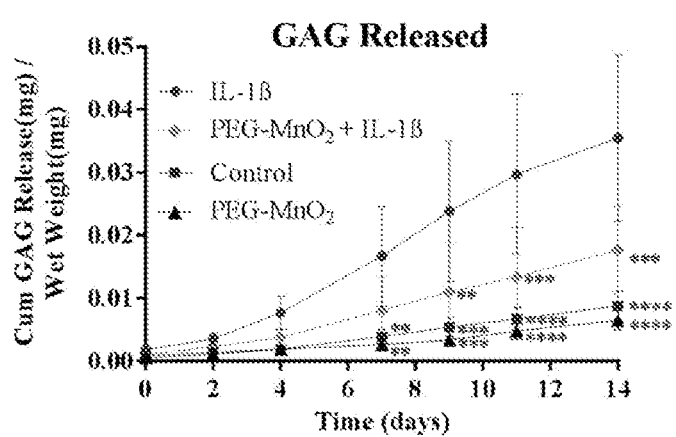
Figure 4D:
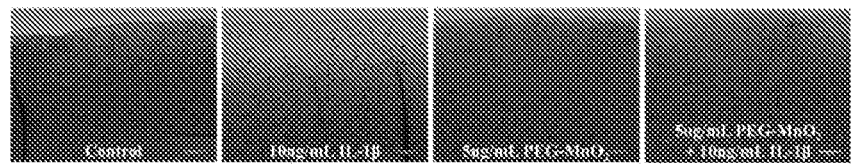
Figure 4E:
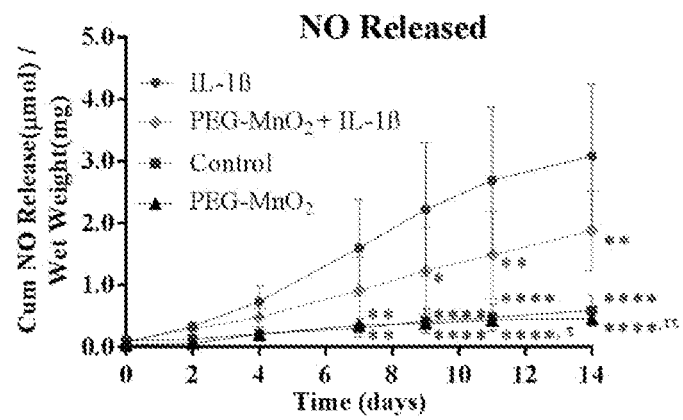

The PEG-$MnO_2$ NPs protected chondrocytes in cartilage explants from IL-1β mediated oxidative stress and apoptosis. IL-1β is a major catabolic cytokine that is involved in the initiation and progression of OA. In OA, pro-inflammatory cytokines stimulate the production of catabolic factors such as MMPs which degrade the ECM of cartilage, leading to the release of GAGs[47]. Moreover, the inducible nitric oxide synthase (iNOS) enzyme is upregulated in osteoarthritic chondrocytes due to stimulation of the cells by mechanical and biochemical factors including inflammatory mediators such as IL-1β and TNF-α [48]. This leads to production of NO within the joint, which acts as a destructive mediator as it activates MMPs, inhibits collagen and proteoglycan synthesis, and induces chondrocyte cell death. Following a 2-week study in which bovine cartilage explants were challenged by 10 ng/mL IL-1β in the presence or absence of 5 ug/mL PEG-$MnO_2$ NPs, the viability of explants was determined using both a LIVE/DEAD staining kit and TUNEL. Both assays showed that while the IL-1β caused significant cell death within the explants, the PEG-$MnO_2$ appears to have mitigated cell death in explants exposed to both IL-1β and PEG-$MnO_2$ (FIGS. 4A and B). The treatment with PEG-$MnO_2$ NPs appears to have improved viability of chondrocytes in cartilage explants over the 2-week study. There was also a 50% decrease in GAG loss in cytokine challenged cartilage explants when treated with PEG-$MnO_2$ (FIG. 4C). This was confirmed by consistent staining of the ECM by Safranin-O in explants treated by both IL-1β and PEG-$MnO_2$ while explants treated with IL-1β alone exhibited decreased staining of ECM due to loss of ECM components from the articular surface (FIG. 4D). PEG-$MnO_2$ NPs also significantly decreased NO production by the cytokine-challenged cartilage explants by 40% (FIG. 4E)

Figures 5G, 5H, 5I:
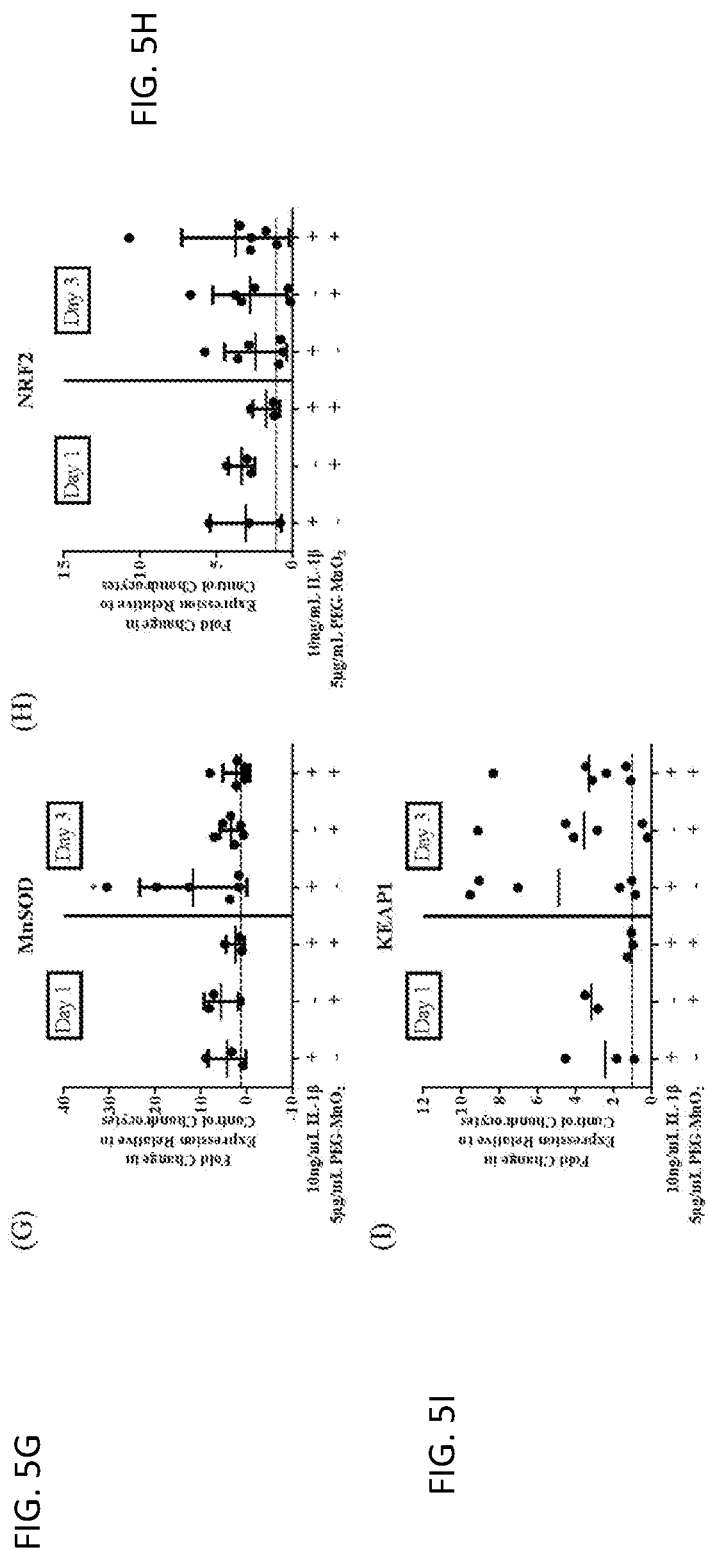

PEG-$MnO_2$ NPs reduced the gene expression of catabolic mediators such as matrix metalloproteinase 3 (MMP3) (FIG. 5A), a disintegrin and metalloproteinase with thrombospondin motifs 4 and 5 (ADAMTS4 and ADAMTS5) (FIGS. 5B and C) and iNOS (FIG. 5D) in bovine chondrocytes exposed to 10 ng/mL IL-1β after 1 day of exposure. The NPs alone also seemed to elicit increased expression of the catabolic mediators by the chondrocytes after 1 day of exposure. This is in line with another study that demonstrated oxidative stress induced DNA damage and apoptosis by $MnO_2$ NPs with human neuronal cells[49]. However, in the longer term, the groups exposed to just the NPs exhibited expression of the catabolic mediators that was similar to control cells. The expression of anti-oxidants such as catalase (CAT) (FIG. 5E), glutathione peroxidase (GPX) (FIG. 5F) and manganese superoxide dismutase (MnSOD) (FIG. 5G) were also downregulated by cytokine-challenged chondrocytes in the presence of PEG-MnO$_2$ NPs. In the longer term, the cells exposed to just the NPs show a decreased expression of the anti-oxidants suggesting the initial upregulation after a day of exposure was a transient effect. Anti-oxidant regulators such as nuclear factor-like 2 (NRF2) (FIG. 5H) and kelch-like ECH-associated protein 1 (KEAP1) (FIG. 5I) were also expressed less by cytokine-challenged cells when exposed to PEG-MnO$_2$ NPs.

Figure 6A:
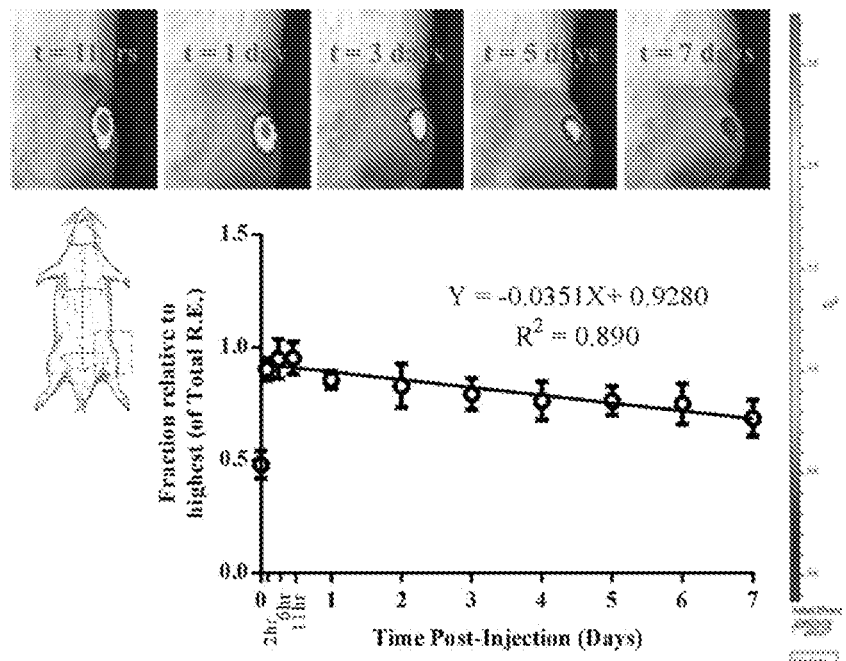
FIGS. 6A-6E. Retention and Cytocompatibility of PEG-$MnO_2$ NPs In Vivo FIG. 6A-After in vivo injection in articular joints of Lewis Rats, $MnO_2$ NPs displayed a linear decline in fluorescent signal with time with 75% of the initial amount of NPs remaining in joints 7 days post-injection.
Figure 6B:
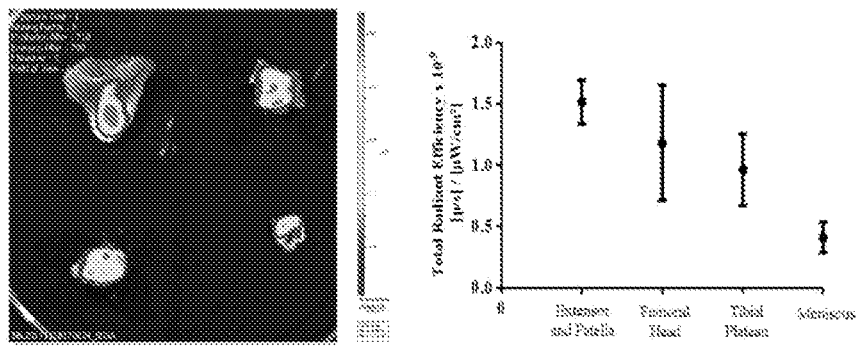
Figure 6C:
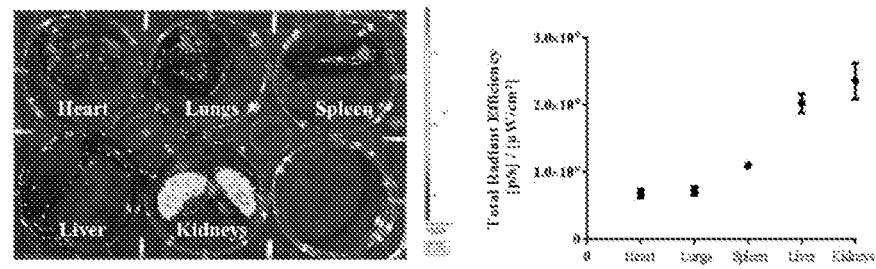
Figures 6D, 6E:
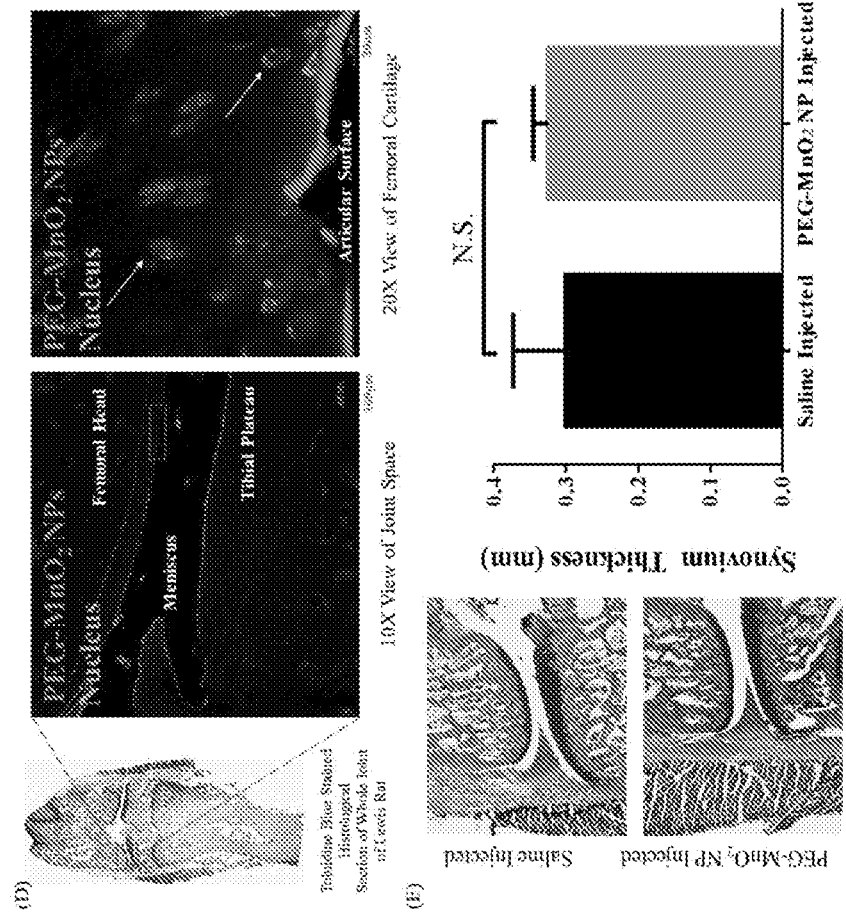

In vivo studies demonstrated joint retention and cartilage localization of the PEG-MnO$_2$ NPs after intra-articular injection in rats. The PEG-MnO$_2$ NPs persisted in the joint space for at least 7 days after in vivo intra-articular injection (FIG. 6A). A persistent challenge with intraarticular therapies is rapid clearance of drugs from the joint space, which undermines therapeutic efficacy. Small molecule drugs are cleared via the synovial vasculature while the lymphatic system removes macromolecules within hours of administration[19]. Despite the small size of the PEG-MnO$_2$ NPs used in this study, they were retained in the joint space for a relatively extended period. Electrostatic interactions with the anionic cartilage matrix may facilitate their joint retention [50,51]. Indeed, ex vivo imaging of joint tissues revealed accumulation of particles at the chondral surfaces (patella, femoral condyles, and tibial plateau) after 11 days (FIG. 6B). Further analysis of the joint confirmed penetration of PEG-MnO$_2$ NPs into cartilage in vivo (FIG. 6C). A gradient of NPs existed in cartilage with the greatest amount of NPs on the articular surface and decreased with depth into the cartilage. The NPs that migrated into the cartilage colocalized with chondrocytes in lacunae (indicated by white arrows in FIG. 6C) and suggests possible uptake of the NPs by the chondrocytes, thereby corroborating in vitro findings. There was minimal accumulation of the NPs in the major organs, including heart, lungs, spleen, liver and kidneys 11 days post-injection (FIG. 6D). Furthermore, histological analysis also revealed no long-term adverse effects of intra-articular MnO$_2$ NP injection into healthy animals. Histological parameters such as synovium thickness (FIG. 6E), total cartilage degeneration width and cartilage matrix loss width were comparable in knees injected with the NPs and those injected with saline after 6 weeks, indicating biocompatibility of the particles in vivo (Table 2).

Example 3: Materials and Methods

Nanoparticle Synthesis and Characterization

MnO$_2$ NPs were synthesized by a 30-minute reduction reaction of potassium permanganate (Acros Organics, Geel, Belgium) with poly(allylamine hydrochloride) (Alfa Aesar, Ward Hill, Mass., USA) in a 1:1 concentration in water [30]. These NPs were further stabilized with an equivalent weight of acrylate-polyethylene glycol succinimidyl valerate (PEG-SVA) of molecular weight 3400 (Laysan Bio Inc., Arab, Ala., USA) in a 2-hour reaction to form PEG-MnO$_2$NPs. Fluorescently tagged particles were synthesized by conjugating the primary amines present on the PEG-MnO$_2$NPs to Alexa Fluor™ 488, 594 or 750 NHS Ester (Succinimidyl Ester) (Life Technologies, Carlsbad, Calif., USA) in the presence of 1-ethyl-3-(3-dimethylaminopropyl)carbodiimide hydrochloride) (EDC) in another 2-hour reaction. Aggregation of PEG-MnO$_2$ NPs in phosphate buffered saline (PBS) and bovine synovial fluid (Animal Technologies, Tyler, Tex., USA) was tested in ratios similar to that used in in vitro studies. The absorption spectra of PEG-SVA, MnO$_2$ NPs and PEG-MnO$_2$ NPs were determined using Fourier-transform infrared spectroscopy (FTIR) (Perkin Elmer Frontier, Perkin Elmer, Waltham, Mass., USA). These PEG-MnO$_2$ NPs were characterized for size and zeta potential by Dynamic Light Scattering (DLS; Particle Sizing Systems, Port Richey, Fla., USA). Measurements for DLS were conducted in water at 0.2 mg/mL for size and zetapotential at room temperature. Distribution analysis was conducted in IGOR Pro version 6.3.7.2 and lognormal distributions were calculated using an algorithm that was previously reported [31]. Imaging of PEG-MnO$_2$ NPs by transmission electron microscopy (TEM) (Tecnai™ FEI Spirit TEM 120 kV, ThermoFisher Scientific, Waltham, Mass., USA) was conducted on negatively stained samples. Analysis of the size of the particles by TEM imaging was analyzed by ImageJ 1.51j8. PEG-MnO$_2$ NPs, in concentrations ranging from 0 to 10 µg/mL, were also characterized for scavenging capacity of 100 µM H$_2$O$_2$ in PBS by a H$_2$O$_2$ colorimetric detection kit (Enzo Life Sciences, Farmingdale, N.Y., USA).

Primary Bovine Cartilage Explants and Cells Extraction

Primary bovine cartilage explants of 4 mm diameter were aseptically harvested from the femoral condyles and patelloformal grooves of male bovine juveniles (Research 87 Inc., Boylston, Mass., USA), and washed in PBS with 1% penicillin-streptomycin. The explants were maintained at 37° C. and 5% carbon dioxide in chondrocyte media (Dulbecco's Modified Eagle Medium (DMEM) with 4.5 g/L glucose, 584 mg/L L-glutamine, 110 mg/L sodium pyruvate, 10 mM hydroxyethyl piperazineethanesulfonic acid (HEPES), 0.1 mM nonessential amino acids, 0.4 mM proline, 50 mg/L vitamin C, 10% fetal bovine serum (FBS), and 1% penicillin-streptomycin). Primary bovine chondrocytes were obtained by 1% trypsin and 1% collagenase II digestion of bovine cartilage explants overnight followed by cell straining.

Cell and Cartilage Explant Uptake of Fluorescently Tagged PEG-MnO$_2$

Primary bovine chondrocytes of Passage 1 were plated on cover slips at 10,000 cells/well seeding density with 0.1 mL chondrocyte media prior to uptake. Once cells reached confluency, Alexa Fluor 488 conjugated PEG-MnO$_2$ NPs were added to the cells at 0, 5, 10 and 20 µg/mL in low serum chondrocyte media (1% FBS) and uptake the NPs by bovine chondrocytes in 2D culture was evaluated by confocal fluorescent imaging (Zeiss LSM 710 Confocal Microscope, Jena, Germany) after 24 hours of incubation. Nuclei was stained with Hoechst 33258, Pentahydrate (bis-Benzimide) (Life Technologies, Carlsbad, Calif., USA) and lysosome stained with CellMask™ Deep Red Plasma membrane Stain (Life Technologies, Carlsbad, Calif., USA). Uptake of the NPs by 3D bovine cartilage explants (through all sides) was also evaluated by adding Alexa Flour 594 conjugated PEG-MnO$_2$ NPs at 0, 5, 50 and 100 µg/mL in low serum chondrocyte media (1% FBS) to the explants. Uptake the NPs by explants was determined by imaging a section through the center of each explant by confocal fluorescent imaging (Zeiss LSM 710 Confocal Microscope, Jena, Germany) after 24 hours of incubation.

Cell and Cartilage Explant Viability in Presence of PEG-MnO$_2$

The cytotoxicity of PEG-MnO$_2$ NPs to primary bovine chondrocytes was tested using a cell proliferation colorimetric assay, CellTiter 96® AQ$^{ueous}$ One Solution Cell Proliferation Assay (MTS) (Promega, Madison, Wis., USA).

Primary bovine chondrocytes of Passage 1 were plated in 96 well plates at 3,000 cells/well seeding density with 0.1 mL chondrocyte media. Once adhered, the cells were incubated in concentrations of PEG-MnO$_2$ NPs ranging from 0 to 100 µg/mL for 24 hours in chondrocyte media. Following this, the cells were washed with PBS once before chondrocyte media was added to the wells for incubation over 48 hours. The chondrocyte media was refreshed in each well 30 minutes prior to adding the MTS reagent. 0.02 mL of MTS reagent was added to the 0.1 mL chondrocyte media in all wells, including control wells that did not contain any cells. 3 hours after addition of the MTS reagent, the media with the MTS reagent from each well was transferred to a different plate and colorimetric analysis was conducted using a spectrophotometer (Biotek Synergy HT, Winooski, Vt., USA) at 490 nm wavelength.

The cytotoxicity of PEG-MnO$_2$ NPs to several other cells that are present in the joint was also determined. The RAW 264.7 Abelson murine leukemia virus transformed macrophage cell line was purchased from American Type Culture Collection (Manassas, Va., USA) and cultured in high glucose Dulbecco's Modified Eagle Medium (DMEM) with 10 mM HEPES and 1% penicillin-streptomycin. RAW 264.7 cells were classically activated using 0.25 ng/mL lipopolysaccharide (Sigma Aldrich, St. Louis, Mo., USA), and 0.5 ng/mL interferon gamma (Sigma Aldrich, St. Louis, Mo., USA). The human bone marrow-derived mesenchymal stem cell line was purchased from ScienCell (Carlsbad, Calif., USA) and cultured in Dulbecco's Modified Eagle Medium (DMEM) with 1 g/L glucose, 584 mg/L L-glutamine, 110 mg/L sodium pyruvate, 10% hyclone fetal bovine serum (FBS), 1% penicillin-streptomycin and 10 ng/uL human recombinant fibroblast growth factor (Peprotech, Rocky Hill, N.J., USA). Primary bovine synoviocytes were obtained by 1% collagenase I digestion of bovine synovium overnight followed by cell straining and cultured in Dulbecco's Modified Eagle Medium (DMEM) with 4.5 g/L glucose, 584 mg/L L-glutamine, 10% fetal bovine serum (FBS), and 1% penicillin-streptomycin.

The viability of cartilage explants following exposure to PEG-MnO$_2$ NPs was determined using a LIVE/DEAD™ Viability/Cytotoxicity Kit for mammalian cells (ThermoFisher, Waltham, Mass., USA). A thin section through the center of each explant was cut and incubated in 0.5 mL of saline containing 4 µM of red-fluorescent ethidium homodimer-1 and 2 µM of green fluorescent calcein-AM for 30 minutes. A z-stack of the fluorescence near the articular surface of each cartilage explant slice was evaluated by confocal fluorescent imaging (Zeiss LSM 710 Confocal Microscope, Jena, Germany).

GAG and NO Measurement

Figure 7:
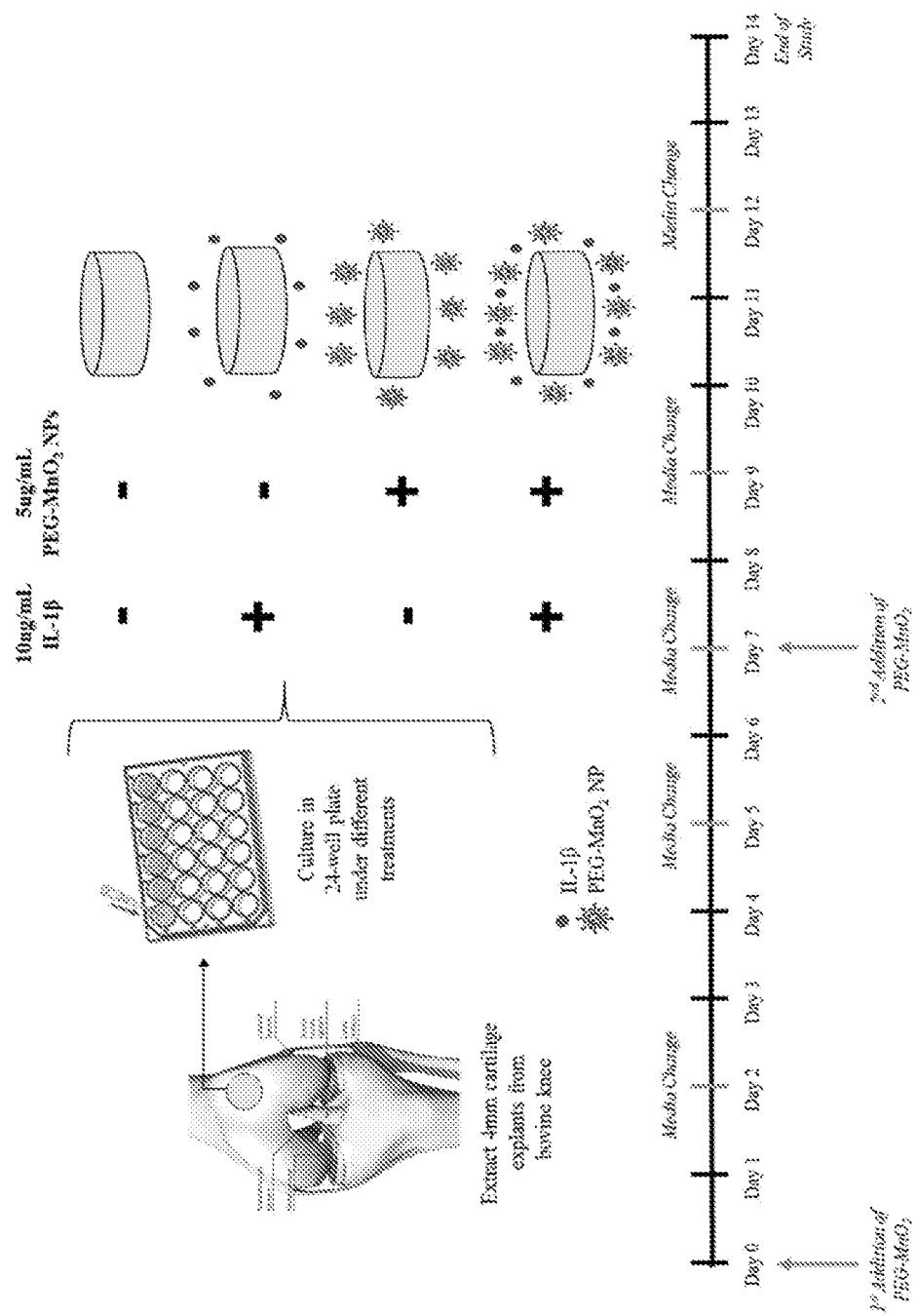

Fresh bovine cartilage explants were incubated in chondrocyte media over a 14-day period and challenged with 10 ng/mL human recombinant IL-1β (Peprotech, Rocky Hill, N.J., USA) in the presence and absence of 5 ug/mL PEG-MnO$_2$NPs. The media was changed every 2-3 days. While the IL-1β was added with every media change for groups exposed to IL-1β, the PEG-MnO$_2$ was only added on Day 0 and 7 for the relevant groups (Scheme 1, FIG. 7). The media in which the explants were incubated was collected and stored at −80° C. following every media change for the period of the experiment. These media samples were tested at the end for concentration of glycosaminoglycans (GAGs), a key component of cartilage extracellular matrix, and concentration of nitric oxide (NO), a key reactive nitrogen species (RNS) related to oxidative stress in OA. The concentration of GAGs in the expended media was quantified using Dimethylmethylene Blue Assay (Sigma Aldrich, St. Louis, Mo., USA) and read using a spectrophotometer (Biotek Synergy HT, Winooski, Vt., USA) at 525 nm wavelength. NO concentrations in the expended media were evaluated by using a Griess Reagent kit (ThermoFisher Scientific, Waltham, Mass., USA) and colorimetrically assessed by spectrophotometer (Biotek Synergy HT, Winooski, Vt., USA) at 528 nm. All absorbances were converted to concentrations using a standard curve and concentrations were normalized by final wet weights of the explants.

Histological Staining

The bovine cartilage explants were fixed in 10% formalin in neutral buffered saline for 24 hours, washed and infused with paraffin, embedded in paraffin and sectioned by the Molecular Pathology Core at University of Florida (Gainesville, Fla., USA). Sections were stained for sulfated glycosaminoglycans using a Safranin-O stain, counter-stained with Fast Green and sealed in Permount (ThermoFisher Scientific, Waltham, Mass., USA). The presence of apoptotic cells within cartilage explants was assessed by Click-iT™ Plus TUNEL Assay for In Situ Apoptosis Detection with Alexa Fluor™ 488 dye (ThermoFisher Scientific, Waltham, Mass., USA).

Quantitative RT-PCR

Figure 8:
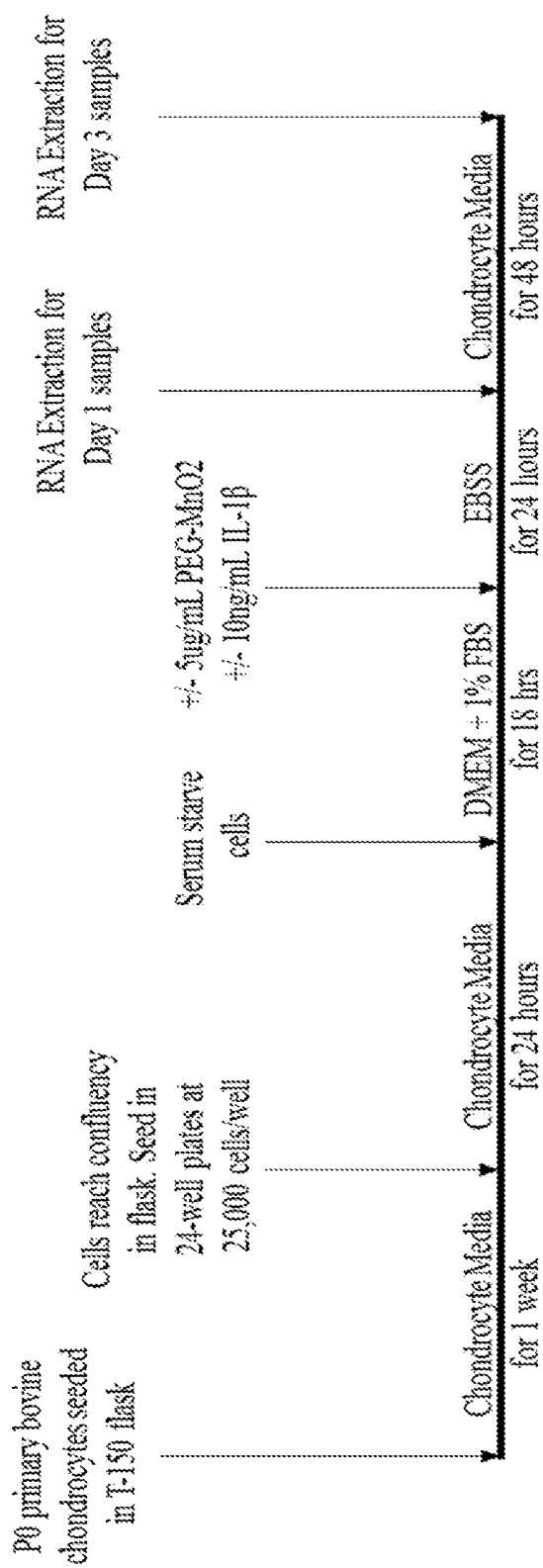

Quantitative gene expression was analyzed in primary bovine chondrocytes challenged with 10 ng/mL human recombinant IL-1β (Peprotech, Rocky Hill, N.J., USA) in the presence and absence of 5 µg/mL PEG-MnO$_2$ NPs. The cells were serum starved for 24 hours in low-serum chondrocyte media (1% FBS) before being exposed to (1) control conditions (2) 10 ng/mL IL-1β (3) 5 ug/mL PEG-MnO$_2$ or (4) 10 ng/mL IL-1β and 5 ug/mL PEG-MnO$_2$ simultaneously in Earle's Balanced Salt Solution (EBSS) for 24 hours. RNA was extracted from Day 1 samples (n=3 per group) while the treatments were removed from Day 3 samples and fresh chondrocyte media was added to them. RNA was extracted from Day 3 samples (n=6 per group) after 48 hours of incubation in chondrocyte media (Scheme 2, FIG. 8). Total RNA was extracted from the cells using RNEasy Mini Kit (Qiagen, Venlo, Netherlands) according to the manufacturer's instructions. RNA samples were reverse transcribed into cDNA in a 20 µL reaction mixture containing 4 µL 5× iScript Reaction Mix, 1 µL iScript Reverse Transcriptase (iScript™ cDNA Synthesis Kit, Bio-Rad, Hercules, Calif., USA), a volume of RNA sample to achieve 400 ng and a volume of nuclease-free water to achieve total volume of 20 uL. The samples were held at 25° C. for 5 min, 46° C. for 20 min and 95° C. for 1 min.

Gene expression levels were quantified by Applied Biosystems™ QuantStudio™ 6 Flex Real-Time PCR System (Applied Biosystems, Life Technologies, Carlsbad, Calif., USA). The assay was performed in a 25 µL reaction mixture containing 10 µL Fast SYBER® Green Master Mix (Applied Biosystems, Life Technologies, Carlsbad, Calif., USA), 1 µL cDNA, 1.25 µL of 5 umol forward primer, 1.25 µL of 5 umol reverse primer and 6.5 µL of nuclease-free water. The sequences for the primers (Eurofins Genomics, Luxembourg City, Luxembourg) used are listed in Table 1. After an initial hold stage at 95° C. for 20 s, cDNA was amplified for 50 cycles at 95° C. for is 60° C. for 20 s, followed by the melt curve stage at 95° C. for 15 s, 60° C. for 1 min and 95° C. for 15 s. Relative expression levels of target genes were determined using the comparative CT method. For each replicate, target gene expression was normalized to bovine 18S. Control bovine chondrocytes were used for baseline gene expression.

TABLE 1

Primer sequences for genes tested with bovine chondrocytes

| Gene | Forward | Reverse |
|---|---|---|
| Matrix Degrading Enzymes | | |
| Bovine MMP3 | 5'-TTCTTCTGGCGGCTGCAT-3' SEQ ID NO: 1 | 5'-GGTTCGGGAGGCACAGATT-3' SEQ ID NO: 2 |
| Bovine ADAMTS-4 | 5'-CTCCATGACAACTCGAAGCA-3' SEQ ID NO: 3 | 5'-CTAGGAGACAGTGCCCGAAG-3' SEQ ID NO: 4 |
| Bovine ADAMTS-5 | 5'-CACCTCAGCCACCATCACAG-3' SEQ ID NO: 5 | 5'-AGTACTCTGGCCCGAAGGTC-3' SEQ ID NO: 6 |
| Bovine iNOS | 5'-GGCAAGCACCACATTGAGA-3' SEQ ID NO: 7 | 5'-TGCGGCTGGATTTCGGA-3' SEQ ID NO: 8 |
| Anti-oxidants | | |
| Bovine CAT | 5'-GAACTGTCCCTACCGT-3' SEQ ID NO: 9 | 5'-TCGTTGGCACTGTTGA-3' SEQ ID NO: 10 |
| Bovine GPX | 5'-GGACTACACCCAGATGAA-3' SEQ ID NO: 11 | 5'-GTGGCGTCGTCACTTG-3' SEQ ID NO: 12 |
| Bovine MnSOD | 5'-GCAAGTAAACCGTCAGC-3' SEQ ID NO: 13 | 5'-AACTACCACCTCCTAGC-3' SEQ ID NO: 14 |
| ROS Modulators | | |
| Bovine NFE2L2 | 5'-CAGCACAACACATACCATCAG-3' SEQ ID NO: 15 | 5'-TGCATGCAGTCATCGAAGTAC-3' SEQ ID NO: 16 |
| Bovine KEAP1 | 5'-TCACCAGGGAAGGATCTACG-3' SEQ ID NO: 17 | 5'-AGCGGCTCAACAGGTACAGT-3' SEQ ID NO: 18 |

In Vivo Retention, Biocompatibility and Biodistribution in Healthy Animals

For all in vivo studies, male Lewis rats (3 months; 250 g) were obtained from Charles River Laboratories (Wilmington, Mass., USA) and allowed to acclimate to the housing at the University of Florida for at least one week prior to any injections or surgeries. All procedures were performed according to the University of Florida Institutional Animal Care and Use Committee (IACUC).

For in vivo joint retention studies, 20 μL intra-articular injections of 5 mg/mL of Alexa Fluor 750 conjugated PEG-MnO$_2$ NPs was conducted on both knees of 3 rats while 1 rat received 20 μL intra-articular injections of saline in both knees and their joint retention was monitored using an in vivo IVIS Spectrum In Vivo Imaging System (Perkin Elmer, Waltham, Mass., USA) over 7 days. The average radiant efficiency of the particles in each left knee was estimated using a region of interest tool. In a separate cohort of 3 animals, at the end of a 11-day study, the knee joints of each rat were dissected and the following components of the knees were imaged to determine distribution of the NPs within the knee joint: extensor mechanism (includes fatpad, patella, synovial bursa, quadriceps), femoral head, tibial plateau and meniscus. Furthermore, biodistribution of the NPs within the rat was determined by imaging the following organs: heart, lungs, spleen, liver and kidneys.

The distribution of the NPs in whole joint histology sections was also evaluated in a separate cohort of 2 rats. 20 μL intra-articular injections of 5 mg/mL of Alexa Fluor 594 conjugated PEG-MnO$_2$ NPs was conducted on 3 knees while 1 knee received a 20 μL intra-articular injection of saline. The rats were euthanized 2 days post-injection and the whole joints from each rat was fixed for 2 days in 10% formalin in neutral buffered saline and decalcified in Cal-Ex for 4 days. The samples were infused with paraffin, embedded in paraffin and sectioned. The distribution of the NPs in whole joint histological sections was visualized using confocal fluorescent imaging (Zeiss LSM 710 Confocal Microscope, Jena, Germany).

Long-term biocompatibility of the NPs in healthy rats was evaluated in another cohort of 3 rats. 20 μL intra-articular injections of 5 mg/mL of Alexa Fluor 750 conjugated PEG-MnO$_2$ NPs was injected into the left knees of the 3 rats. After 6 weeks, the animals were euthanized and the whole joints were processed as mentioned previously to obtain whole joint sections. These sections were stained by Toluidine Blue and a Gerwin evaluation [32] was conducted by a blinded investigator using GEKO software, an open source tool developed by the Orthopaedic Biomedical Engineering Laboratory at University of Florida for evaluation of knee OA [33]. A saline injected knee from the whole joint distribution study was used as a control.

Statistics

Statistical analysis was conducted in GraphPad PRISM 7.01 (La Jolla, Calif., USA). Error bars indicate standard deviations. For the in vitro proliferation studies, a Dunnett's test was conducted while statistical comparison of means was conducted in GraphPad via Two-way ANOVA with Tukey's multiple comparisons tests for all other studies.

TABLE 2

Cytocompatibility of PEG-MnO$_2$ NPs In Vivo. This table contains all the parameters of evaluation of knee OA using GEKO software. Saline injected knees and knees 7 weeks after injection of PEG-MnO$_2$ were evaluated on this software and compared. Non- significant differences were found between the saline injected knees and PEG-MnO$_2$ injected knees for osteophyte size, synovium thickness, cartilage matrix loss width 0%, 50% and 100% lesion depth, total cartilage degeneration width, significant cartilage degeneration width, zone 1, 2 and 3 depth ratio of lesion. This evaluation revealed minimal long-term cytocompatibility of the particles.

| Parameter | Saline Injected Knees | PEG-MnO$_2$ Knees |
|---|---|---|
| Medial Compartment Tibial Plateau Width (mm) | 1.92 (±0.14) | 1.98 (±0.07) |
| Osteophyte Size (mm) | 0.16 (±0.03) | 0.02 (±0.04) |
| Synovium Thickness (mm) | 0.30 (±0.07) | 0.33 (±0.02) |
| Cartilage Matrix Loss Width 0% Lesion Depth (mm) | 0 | 0 |
| Cartilage Matrix Loss Width 50% Lesion Depth (mm) | 0 | 0 |
| Cartilage Matrix Loss Width 100% Lesion Depth (mm) | 0 | 0 |
| Total Cartilage Degeneration Width (% of Tibial Plateau)(mm) | 0 | 0 |
| Significant Cartilage Degeneration Width (% of Tibial Plateau)(mm) | 0 | 0 |
| Zone 1 (Medial) Zonal Depth Ratio of Lesion (% Full Cartilage Thickness) | 0 | 0 |
| Zone 2 (Central) Zonal Depth Ratio of Lesion (% Full Cartilage Thickness) | 0 | 0 |
| Zone 3 (Lateral) Zonal Depth Ratio of Lesion (% Full Cartilage Thickness) | 0 | 0 |

REFERENCES

References listed below and throughout the specification are hereby incorporated by reference in their entirety.

[1] R. C. Lawrence, Estimates of the Prevalence of Arthritis and Other Rheumatic Conditions in the United States, Part II, Arthritis Rheum. 58 (2008) 26-35. doi:10.1002/art.23176.Estimates.

[2] J. M. Hootman, C. G. Helmick, Projections of US prevalence of arthritis and associated activity limitations, Arthritis Rheum. 54 (2006) 226-229. doi:10.1002/art.21562.

[3] A. K. Grover, S. E. Samson, Benefits of antioxidant supplements for knee osteoarthritis: Rationale and reality, Nutr. J. 15 (2016). doi:10.1186/s12937-015-0115-z.

[4] J. A. Collins, B. O. Diekman, R. F. Loeser, Targeting aging for disease modification in osteoarthritis, Curr. Opin. Rheumatol. 30 (2018) 101-107. doi:10.1097/BOR.0000000000000456.

[5] P. Lepetsos, A. G. Papavassiliou, ROS/oxidative stress signaling in osteoarthritis, Biochim. Biophys. Acta—Mol. Basis Dis. 1862 (2016) 576-591. doi:10.1016/j.bbadis.2016.01.003.

[6] E. Regan, J. Flannelly, R. Bowler, K. Tran, M. Nicks, B. D. Carbone, D. Glueck, H. Heijnen, R. Mason, J. Crapo, Extracellular superoxide dismutase and oxidant damage in osteoarthritis, Arthritis Rheum. 52 (2005) 3479-3491. doi:10.1002/art.21387.

[7] J. W. J. Bijlsma, F. Berenbaum, F. P. J. G. Lafeber, Osteoarthritis: An update with relevance for clinical practice, Lancet. 377 (2011) 2115-2126. doi:10.1016/S0140-6736(11)60243-2.

[8] R. F. Loeser, Aging processes and the development of osteoarthritis, Curr. Opin. Rheumatol. 25 (2013) 108-113. doi:10.1097/BOR.0b013e32835a9428.

[9] H. I. Roach, The complex pathology of osteoarthritis: Even mitochondria are involved, Arthritis Rheum. 58 (2008) 2217-2218. doi:10.1002/art.23635.

[10] R. F. Loeser, J. A. Collins, B. O. Diekman, Ageing and the pathogenesis of osteoarthritis, Nat. Rev. Rheumatol. 12 (2016) 412-420. doi:10.1038/nrrheum.2016.65.

[11] J. A. Buckwalter, D. D. Anderson, T. D. Brown, Y. Tochigi, J. A. Martin, The Roles of Mechanical Stresses in the Pathogenesis of Osteoarthritis: Implications for Treatment of Joint Injuries, Cartilage. 4 (2013) 286-294. doi:10.1177/1947603513495889.

[12] C. C. Rosenbaum, D. P. O'Mathuna, M. Chavez, K. Shields, Antioxidants and antiinflammatory Dietary Supplements for Osteoarthritis—American Family Physician, Altern. Ther. 16 (2010) 32-40. http://www.aafp.org/afp/2008/0115/p177.html.

[13] P. H. Canter, B. Wider, E. Ernst, The antioxidant vitamins A, C, E and selenium in the treatment of arthritis: A systematic review of randomized clinical trials, Rheumatology. 46 (2007) 1223-1233. doi:10.1093/rheumatology/kem116.

[14] T. Takada, S. Miyaki, H. Ishitobi, Y. Hirai, T. Nakasa, K. Igarashi, M. K. Lotz, M. Ochi, Bach1 deficiency reduces severity of osteoarthritis through upregulation of heme oxygenase-1, Arthritis Res. Ther. 17 (2015) 1-11. doi:10.1186/s13075-015-0792-1.

[15] F. Rousset, M. V. C. Nguyen, L. Grange, F. Morel, B. Lardy, Heme Oxygenase-1 Regulates Matrix Metalloproteinase MMP-1 Secretion and Chondrocyte Cell Death via Nox4 NADPH Oxidase Activity in Chondrocytes, PLoS One. 8 (2013). doi:10.1371/journal.pone.0066478.

[16] R. A. Greenwald, Therapeutic benefits of oxygen radical scavenger treatments remain unproven, J. Free Radicals Biol. Med. 1 (1985) 173-177. doi:10.1016/0748-5514(85)90115-1.

[17] R. A. Greenwald, Oxygen radicals, inflammation, and arthritis: Pathophysiological considerations and implications for treatment, Semin. Arthritis Rheum. 20 (1991) 219-240. doi:10.1016/0049-0172(91)90018-U.

[18] W. Gammer, L.-G. Broback, Clinical Comparison of Orgotein and Methylpredisolone acetate in the Treatment of Osteoarthrosis of the Knee Joint, Scand. J. Rheumatol. 13 (1984) 108-112. doi:10.3109/03009748409100372.

[19] C. Evans, V. Kraus, L. Setton, Progress in intra-articular therapy, Rheumatol, Nat Rev. 10 (2015) 11-22.

[20] D. B. Broughton, R. L. Wentworth, M. E. Laing, Mechanism of Decomposition of Hydrogen Peroxide Solutions with Manganese Dioxide. II, J. Am. Chem. Soc. 69 (1947) 744-747. doi:10.1021/ja01196a004.

[21] P. J. Moulton, T. S. Hiran, M. B. Goldring, J. T. Hancock, Detection of protein and mRNA of various components of the NADPH oxidase complex in an immortalized human chondrocyte line, Br J Rheumatol. 36 (1997) 522-529.

[22] T. S. Hiran, P. J. Moulton, J. T. Hancock, Detection of superoxide and NAPDH oxidase in porcine articular chondrocytes, Free Radic. Biol. Med. 23 (1997) 736-743. doi:10.1016/S0891-5849(97)00054-3.

[23] J. Bizeau, C. Tapeinos, C. Marella, A. Larrañaga, A. Pandit, Synthesis and characterization of hyaluronic acid coated manganese dioxide microparticles that act as ROS scavengers, Colloids Surfaces B Biointerfaces. 159 (2017) 30-38. doi:10.1016/j.colsurfb.2017.07.081.

[24] A. Z. Abbasi, C. R. Gordijo, M. A. Amini, A. Maeda, A. M. Rauth, R. S. DaCosta, X. Y. Wu, Hybrid manganese dioxide nanoparticles potentiate radiation therapy by modulating tumor hypoxia, Cancer Res. 76 (2016) 6643-6656. doi:10.1158/0008-5472.CAN-15-3475.

[25] P. Prasad, C. R. Gordijo, A. Z. Abbasi, A. Maeda, A. Ip, A. M. Rauth, R. S. Dacosta, X. Y. Wu, Multifunctional albumin-$MnO_2$ nanoparticles modulate solid tumor microenvironment by attenuating hypoxia, acidosis, vascular endothelial growth factor and enhance radiation response, ACS Nano. 8 (2014) 3202-3212. doi:10.1021/nn405773r.

[26] W. Zhu, Z. Dong, T. Fu, J. Liu, Q. Chen, Y. Li, R. Zhu, L. Xu, Z. Liu, Modulation of Hypoxia in Solid Tumor Microenvironment with $MnO_2$Nanoparticles to Enhance Photodynamic Therapy, Adv. Funct. Mater. 26 (2016) 5490-5498. doi:10.1002/adfm.201600676.

[27] M. Zhang, L. Xing, H. Ke, Y. J. He, P. F. Cui, Y. Zhu, G. Jiang, J. Bin Qiao, N. Lu, H. Chen, H. L. Jiang, $MnO_2$-Based Nanoplatform Serves as Drug Vehicle and MRI Contrast Agent for Cancer Theranostics, ACS Appl. Mater. Interfaces. 9 (2017) 11337-11344. doi:10.1021/acsami.6b15247.

[28] M. Song, T. Liu, C. Shi, X. Zhang, X. Chen, Bioconjugated manganese dioxide nanoparticles enhance chemotherapy response by priming tumor-Associated macrophages toward ml-like phenotype and attenuating tumor hypoxia, ACS Nano. 10 (2016) 633-647. doi:10.1021/acsnano.5b06779.

[29] M. H. Tootoonchi, M. Hashempour, P. L. Blackwelder, C. A. Fraker, Manganese oxide particles as cytoprotective, oxygen generating agents, Acta Biomater. 59 (2017) 327-337. doi:10.1016/j.actbio.2017.07.006.

[30] Y. Luo, Preparation of MnO2 nanoparticles by directly mixing potassium permanganate and polyelectrolyte aqueous solutions, Mater. Lett. 61 (2007) 1893-1895. doi:10.1016/j.matlet.2006.07.165.

[31] A. C. Bohorquez, C. Rinaldi, In situ evaluation of nanoparticle-protein interactions by dynamic magnetic susceptibility measurements, Part. Part. Syst. Charact. 31 (2014) 561-570. doi:10.1002/ppsc.201300296.

[32] N. Gerwin, A. M. Bendele, S. Glasson, C. S. Carlson, The OARSI histopathology initiative—recommendations for histological assessments of osteoarthritis in the rat, Osteoarthr. Cartil. 18 (2010) S24-S34. doi:10.1016/j.joca.2010.05.030.

[33] H. E. Kloefkorn, B. Y. Jacobs, D. F. Xie, K. D. Allen, A graphic user interface for the evaluation of knee osteoarthritis (GEKO): an open-source tool for histological grading, Osteoarthr. Cartil. 27 (2018) 114-117. doi:10.1016/j.joca.2018.09.005.

[34] D. Rothenfluh, H. Bermudez, C. P. O'Neil, J. Hubbell, Biofunctional polymer nanoparticles for intra-articular targeting and retention in cartilage. Nat. Mater. 7 (2008) 248-254. doi:10.1038/nmat2116.

[35] J. R. Levick, Flow through interstitium and other fibrous matrices, Q. J. Exp. Physiol. 72 (1987) 409-437. doi:10.1113/expphysiol.1987.sp003085.

[36] P. A. Torzilli, J. M. Arduino, J. D. Gregory, M. Bansal, Effect of proteoglycan removal on solute mobility in articular cartilage. J. Biomech. 30 (1997) 895-902.

[37] S. Dey, A. Sidor, B. O'Rourke, Compartment-specific control of reactive oxygen species scavenging by antioxidant pathway enzymes, J. Biol. Chem. 291 (2016) 11185-11197. doi:10.1074/jbc.M116.726968.

[38] D. Han, F. Antunes, R. Canali, D. Rettori, E. Cadenas, Voltage-dependent anion channels control the release of the superoxide anion from mitochondria to cytosol, J. Biol. Chem. 278 (2003) 5557-5563. doi:10.1074/jbc.M210269200.

[39] H. J. Forman, M. Tones, Redox signaling in macrophages, Mol. Aspects Med. 22 (2001) 189-216. doi:10.1016/S0098-2997(01)00010-3.

[40] A. Covarrubias, V. Byles, T. Horng, ROS sets the stage for macrophage differentiation, Cell Res. 23 (2013) 984-985. doi:10.1038/cr.2013.88.

[41] H. Tan, N. Wang, S. Li, M. Hong, X. Wang, Y. Feng, The Reactive Oxygen Species in Macrophage Polarization: Human Diseases, 2016 (2016). doi:10.1155/2016/2795090.

[42] J. Canton, R. Khezri, M. Glogauer, S. Grinstein, Contrasting phagosome pH regulation and maturation in human M1 and M2 macrophages, Mol. Biol. Cell. 25 (2014) 3330-3341. doi:10.1091/mbc.E14-05-0967.

[43] M. A. Cassatella, F. Bazzoni, R. M. Flynn, S. Dusi, G. Trinchieri, F. Rossi, Molecular basis of interferon-g and lipopolysaccharide enhancement of phagocyte respiratory burst capability, J. Biol. Chem. 265 (1990) 20241-20246.

[44] A. J. Croft, S. Metcalfe, K. Honma, J. G. Kay, Macrophage polarization alters postphagocytosis survivability of the commensal *Streptococcus gordonii*, Infect. Immun. 86 (2018). doi:10.1128/IAI.00858-17.

[45] A.-J. Casbon, M. E. Long, K. W. Dunn, L.-A. H. Allen, M. C. Dinauer, Effects of IFN- on intracellular trafficking and activity of macrophage NADPH oxidase flavocytochrome b558, J. Leukoc. Biol. 92 (2012) 869-882. doi:10.1189/jlb.0512244.

[46] P. E. Newburger, Q. Dai, C. Whitney, In vitro regulation of human phagocyte cytochrome b heavy and light chain gene expression by bacterial lipopolysaccharide and recombinant human cytokines, J. Biol. Chem. 266 (1991) 16171-16177. doi:10.1002/mrd.20316.

[47] M. Daheshia, J. Q. Yao, The interleukin 1β pathway in the pathogenesis of osteoarthritis, J. Rheumatol. 35 (2008) 2306-2312. doi:10.3899/jrheum.080346.

[48] S. B. Abramson, Osteoarthritis and nitric oxide, Osteoarthr. Cartil. 16 (2008). doi:10.1016/S1063-4584(08)60008-4.

[49] S. Alarifi, D. Ali, S. Alkahtani, Oxidative Stress-Induced DNA Damage by Manganese Dioxide Nanoparticles in Human Neuronal Cells, Biomed Res. Int. 2017 (2017). doi:10.1155/2017/5478790.

[50] S. Brown, J. Pistiner, I. Adjei, B. Sharma, Nanoparticle properties for delivery to cartilage: the implications of disease state, synovial fluid, and off-target uptake, Mol. Pharm. (2017) acs.molpharmaceut.7b00484. doi:10.1021/acs.molpharmaceut.7b00484.

[51] A. G. Bajpayee, C. R. Wong, M. G. Bawendi, E. H. Frank, A. J. Grodzinsky, Avidin as a model for charge driven transport into cartilage and drug delivery for treating early stage post-traumatic osteoarthritis, Biomaterials. 35 (2014) 538-549. doi:10.1016/j.biomaterials.2013.09.091.

What is claimed is:

1. A method of treating osteoarthritis in the joint of a subject in need thereof, comprising injecting the joint intra-articularly with a manganese dioxide nanoparticle formulation, wherein the manganese dioxide nanoparticle formulation comprises:
   (a) a plurality of manganese dioxide nanoparticles having a size by transmission electron microscopy of about 5 to about 30 nm;
   (b) a stabilizer comprising succinimidyl valerate poly(ethylene glycol); and
   (c) an aqueous pharmaceutically acceptable carrier for injection.

2. The method of claim 1, wherein the manganese dioxide nanoparticle formulation inhibits glycosaminoglycan loss in cartilage in the joint.

3. The method of claim 1, wherein the manganese dioxide nanoparticle formulation reduces nitric oxide in cartilage in the joint.

4. A manganese dioxide nanoparticle, which is produced by
   (a) adding poly(allylamine hydrochloride) and KMnO4 in a 1:1 ratio to water with mixing;
   (b) washing the nanoparticles formed and suspending the nanoparticles in water;
   (c) adding succinimidyl valerate poly(ethylene glycol) to the nanoparticles, with further mixing; and
   (d) washing the nanoparticles.

5. The manganese dioxide nanoparticle of claim 4 which has a size of about 5 nm to about 30 nm by transmission electron microscopy or a size of about 15 nm to about 200 nm by dynamic light scattering.

6. The manganese dioxide nanoparticle of claim 4 which has a size of about 15 nm by transmission electron microscopy or a size of about 67 nm by dynamic light scattering.

7. A manganese dioxide nanoparticle formulation, comprising the manganese dioxide nanoparticle of claim 4 and a pharmaceutically acceptable carrier.

8. A manganese dioxide nanoparticle formulation, comprising
   (a) a plurality of manganese dioxide nanoparticles having a size by transmission electron microscopy of about 5-30 nm;
   (b) a stabilizer comprising succinimidyl valerate poly (ethylene glycol); and
   (c) an aqueous pharmaceutically acceptable carrier.

9. A method of treating oxidative stress in a subject in need thereof, comprising administering to the subject the manganese dioxide nanoparticle of claim 4.

10. A method of treating oxidative stress in a subject in need thereof, comprising administering to the subject the manganese dioxide nanoparticle formulation of claim 7.

11. A method of treating oxidative stress in a subject in need thereof, comprising administering to the subject the manganese dioxide nanoparticle formulation of claim 8.

12. The method of claim 7 wherein the subject is a mammal.

13. The method of claim 12 wherein the subject is a human.

14. The method of claim 10 wherein the subject suffers from osteoarthritis.

15. The method of claim 11 wherein the subject suffers from osteoarthritis.

16. The method of claim 10 wherein the administration is by intra-articular injection.

17. The method of claim 11 wherein the administration is by intra-articular injection.

18. A method of scavenging reactive oxygen species in a tissue, comprising contacting the tissue with the manganese dioxide nanoparticle of claim 4.

19. A method of treating osteoarthritis in a subject in need thereof, comprising administering to the subject the manganese dioxide nanoparticle formulation of claim 7.

20. A method of treating osteoarthritis in a subject in need thereof, comprising administering to the subject the manganese dioxide nanoparticle formulation of claim 8.

21. A scaffold or substrate comprising the nanoparticles of claim 4.

* * * * *

SEQUENCE LISTING

```
<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
ttcttctggc ggctgcat                                                 18

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
ggttcgggag gcacagatt                                                19

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ctccatgaca actcgaagca                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctaggagaca gtgcccgaag                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cacctcagcc accatcacag                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
agtactctgg cccgaaggtc                                               20

<210> SEQ ID NO 7
<211> LENGTH: 19
<212> TYPE: DNA
<213> ORGANISM: Artificial Sequence
```

```
<220> FEATURE:
<223> OTHER INFORMATION: primer

<400> SEQUENCE: 7
ggcaagcacc acattgaga                                                  19

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8
tgcggctgga tttcgga                                                    17

<210> SEQ ID NO 9
<211> LENGTH: 16
<212> TYPE: DNA
<213> ORGANISM: Artificial Sequence
<220> FEATURE:
<223> OTHER INFORMATION: primer

<400> SEQUENCE: 9
gaactgtccc taccgt                                                     16

<210> SEQ ID NO 10
<211> LENGTH: 16
<212> TYPE: DNA
<213> ORGANISM: Artificial Sequence
<220> FEATURE:
<223> OTHER INFORMATION: primer

<400> SEQUENCE: 10
tcgttggcac tgttga                                                     16

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ggactacacc cagatgaa                                                   18

<210> SEQ ID NO 12
<211> LENGTH: 16
<212> TYPE: DNA
<213> ORGANISM: Artificial Sequence
<220> FEATURE:
<223> OTHER INFORMATION: primer

<400> SEQUENCE: 12
gtggcgtcgt cacttg                                                     16

<210> SEQ ID NO 13
<211> LENGTH: 17
<212> TYPE: DNA
<213> ORGANISM: Artificial Sequence
<220> FEATURE:
<223> OTHER INFORMATION: primer

<400> SEQUENCE: 13
gcaagtaaac cgtcagc                                                    17
```

```
<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
aactaccacc tcctagc                                                    17

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
cagcacaaca cataccatca g                                               21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
tgcatgcagt catcgaagta c                                               21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cagcacaaca cataccatca g                                               21

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agcggctcaa caggtacagt                                                 20
```